(12) United States Patent
Clarkin et al.

(10) Patent No.: US 10,149,861 B2
(45) Date of Patent: Dec. 11, 2018

(54) GALLIUM-BASED GLASS COMPOSITION

(71) Applicant: DUBLIN CITY UNIVERSITY, Dublin (IE)

(72) Inventors: Owen Clarkin, Wexford (IE); Caitriona Lally, Dublin (IE)

(73) Assignee: DUBLIN CITY UNIVERSITY, Dublin (IE)

( * ) Notice: Subject to any disclaimer, the term of this patent is extended or adjusted under 35 U.S.C. 154(b) by 59 days.

(21) Appl. No.: 15/517,894

(22) PCT Filed: Oct. 9, 2015

(86) PCT No.: PCT/EP2015/073477
§ 371 (c)(1),
(2) Date: Apr. 7, 2017

(87) PCT Pub. No.: WO2016/055650
PCT Pub. Date: Apr. 14, 2016

(65) Prior Publication Data
US 2017/0239292 A1    Aug. 24, 2017

(30) Foreign Application Priority Data
Oct. 10, 2014 (GB) .................................. 1417984.0

(51) Int. Cl.
*A61K 33/24* (2006.01)
*A61K 9/00* (2006.01)
(Continued)

(52) U.S. Cl.
CPC ............ *A61K 33/24* (2013.01); *A61K 9/0024* (2013.01); *A61K 33/00* (2013.01); *A61K 33/06* (2013.01); *A61K 33/08* (2013.01); *A61K 33/10* (2013.01); *A61K 33/42* (2013.01); *A61K 47/12* (2013.01); *A61K 47/36* (2013.01); *A61L 24/0015* (2013.01); *A61L 24/0031* (2013.01);
(Continued)

(58) Field of Classification Search
CPC ...... A61K 33/24; A61K 9/0024; A61K 33/06; A61K 33/00; A61K 33/08; A61K 33/10; A61K 33/42; A61K 47/12; A61K 47/36; A61L 24/0015; A61L 24/0031; A61L 24/0084; A61L 24/0089; A61L 24/02; A61L 24/08; A61L 27/10; A61L 27/20; A61L 27/446; A61L 27/46; A61L 27/507; A61L 27/52; A61L 27/54; A61L 31/026; A61L 31/128; A61L 2300/404; A61L 2400/06; A61L 2430/36; A61M 25/1018; C03C 3/11; C03C 4/0007; C03C 4/0035; C03C 14/008; C03C 2214/12; C03C 2214/17; C08K 3/40
See application file for complete search history.

(56) References Cited

U.S. PATENT DOCUMENTS

| | | |
|---|---|---|
| 2003/0100942 A1 | 5/2003 | Ken et al. |
| 2004/0081706 A1 | 4/2004 | Trainer et al. |
| 2009/0053318 A1 | 2/2009 | Tan et al. |

OTHER PUBLICATIONS

Alhalawani et al., "Influence of Gallium on the Surface Properties of Zinc Based Glass Polyalkenoate Cements," *Materials Chemistry and Physics* 147:360-364, 2014.
(Continued)

*Primary Examiner* — Trevor Love
(74) *Attorney, Agent, or Firm* — Cozen O'Connor

(57) ABSTRACT

A gallium silica glass composition is described. The glass can be used in variety of biomedical applications.

25 Claims, 16 Drawing Sheets

(51) Int. Cl.
| | |
|---|---|
| A61K 33/00 | (2006.01) |
| A61K 33/06 | (2006.01) |
| A61K 33/08 | (2006.01) |
| A61K 33/10 | (2006.01) |
| A61K 33/42 | (2006.01) |
| A61K 47/12 | (2006.01) |
| A61K 47/36 | (2006.01) |
| A61L 24/00 | (2006.01) |
| A61L 24/02 | (2006.01) |
| A61L 24/08 | (2006.01) |
| A61L 27/10 | (2006.01) |
| A61L 27/20 | (2006.01) |
| A61L 27/44 | (2006.01) |
| A61L 27/46 | (2006.01) |
| A61L 27/50 | (2006.01) |
| A61L 27/52 | (2006.01) |
| A61L 27/54 | (2006.01) |
| A61K 31/02 | (2006.01) |
| A61K 31/12 | (2006.01) |
| A61M 25/10 | (2013.01) |
| C03C 3/11 | (2006.01) |
| C03C 4/00 | (2006.01) |
| C03C 14/00 | (2006.01) |
| C08K 3/40 | (2006.01) |
| A61L 31/02 | (2006.01) |
| A61L 31/12 | (2006.01) |

(52) U.S. Cl.
CPC ....... *A61L 24/0084* (2013.01); *A61L 24/0089* (2013.01); *A61L 24/02* (2013.01); *A61L 24/08* (2013.01); *A61L 27/10* (2013.01); *A61L 27/20* (2013.01); *A61L 27/446* (2013.01); *A61L 27/46* (2013.01); *A61L 27/507* (2013.01); *A61L 27/52* (2013.01); *A61L 27/54* (2013.01); *A61L 31/026* (2013.01); *A61L 31/128* (2013.01); *A61M 25/1018* (2013.01); *C03C 3/11* (2013.01); *C03C 4/0007* (2013.01); *C03C 4/0035* (2013.01); *C03C 14/008* (2013.01); *C08K 3/40* (2013.01); *A61L 2300/404* (2013.01); *A61L 2400/06* (2013.01); *A61L 2430/36* (2013.01); *C03C 2214/12* (2013.01); *C03C 2214/17* (2013.01)

(56) References Cited

OTHER PUBLICATIONS

Branda et al., "Effect of the Substitution of $M_2O_3$ (M=La, Y, In, Ga, Al) for CaO on the Bioactivity of $2.5CaO \cdot 2SiO_2$ Glass," *Biomaterials* 23:711-716, 2002.

Franchini et al., "Gallium-Containing Phospho-silicate Glasses: Synthesis and in vitro Bioactivity," *Materials Science and Engineering C* 32:1401-1406, 2012.

Lusvardi et al., "Gallium-Containing Phophosilicate Glasses: Functionalization and in-vitro Bioactivity," *Materials Science and Engineering C* 33:3190-3196, 2013.

Mouriño et al., "Preparation and Characterization of Gallium Releasing 3-D Alginate Coated 45S5 Bioglass® Based Scaffolds for Bone Tissue Engineering," *Advanced Engineering Materials* 12(7):B283-B291, 2010.

Mouriño et al., "Physiocochemical, Biological and Drug-Release Properties of Gallium Crosslinked Alginate/Nanoparticulate Bioactive Glass Composite Films," *Soft Matter* 7:6705-6712, 2011.

Salinas et al. "Substitutions of Cerium, Gallium and Zinc in Ordered Mesoporous Bioactive Glasses," *Acta Biomaterialia* 7:3452-3458, 2011.

Shruti et al., "Mesoporous Bioactive Scaffolds Prepared with Cerium-, Gallium- and Zinc-Containing Glasses," *Acta Biomaterialia* 9:4836-4844, 2013.

Shruti et al., "Curcumin Release from Cerium, Gallium and Zinc Containing Mesoporous Bioactive Glasses,"*Microporous and Mesoporous Materials* 180:92-101, 2013.

Valappil et al., "Controlled Delivery of Antimicrobial Gallium Ions from Phosphate-Based Glasses," *Acta Biomaterialia* 5:1198-1210, 2009.

Wren et al., "Gallium Containing Glass Polyalkenoate Anti-Cancerous Bone Cements: Glass Characterization and Physical Properties," *J Mater Sci: Mater Med* 23:1823-1833, 2012.

Combined Search and Examination Report, dated Apr. 13, 2015, for GB 1417984.0, 8 pages.

International Search Report, dated Dec. 7, 2015, for PCT/EP2015/073477, 5 pages.

Written Opinion, dated Dec. 7, 2015, for PCT/EP2015/073477, 9 pages.

International Preliminary Report on Patentability dated Apr. 11, 2017, for corresponding International Application No. PCT/EP2015/073477, 10 pages.

Dusseault et al., "Evaluation of alginate purification methods: Effect on polyphenol, endotoxin, and protein contamination," *J. Biomed Mater Res* 76A:243-251, 2006.

Jork et al., "Biocompatible alginate from freshly collected *Laminaria pallida* for implantation," *Appl Microbiol. Biotechnol* 53:224-229, 2000.

Klöck et al., "Production of purified alginates suitable for use in immunoisolated transplantation,"*Appl. Microbiol. Biotechnol.* 40:638-643, 1994.

Zimmermann et al., "Production of mitogen-contamination free alginates with variable ratios of mannuronic acid to guluronic acid by free flow electrophoresis," *Electrophoresis* 13:269-274, 1992.

GALLIUM-BASED GLASS COMPOSITION

FIELD OF THE INVENTION

The present invention relates to glass compositions and particularly to glass compositions that are usefully employed in medical applications. The glass can be combined with a polymeric solution so as to allow it be provided in a gelling form or as a gelled or set scaffold, for example for use in adhesive, embolization, filler or tissue engineering applications or to deliver some therapeutic value. An exemplary gallium based glass composition in accordance with the present teaching is provided in a hydrogel matrix and used to correct defects in a vascular network such as the treatment of aneurysms.

BACKGROUND

An aneurysm is a localized dilation of a blood vessel wall which, if untreated, can rupture causing internal haemorrhaging, resulting in disability or death. Aneurysms are caused by degradation of the vessel wall due to atherosclerosis or infection. Cerebral aneurysms cause 32,000 deaths each year in the USA. In the case of cerebral aneurysms, haemorrhaging often triggers vasospasm. Vasospasm is a spasmodic contraction of the vessel wall, which results in constriction of blood flow to the brain. Vasospasm occurs in 50% of patients and accounts for 25% of severe disability and death.

Industries, in recent years, have looked to improve the current platinum endovascular embolization devices by coating them with hydrogels, aimed at improving the percentage fill of the aneurysm and reducing incidences of postoperative re-canalisation (reopening of the aneurysm to blood flow). In addition to this, surgeons have begun looking towards glues and embolization agents for the treatment of aneurysms, both for wide-neck aneurysms which cannot be filled using coils, and for more common aneurysm geometries due to their ability to more completely fill the aneurysm without leaving spaces which can become pressurised, resulting in re-canalisation. However, currently embolization agents are less than ideal and incidences of post-surgical complications, severe disability and death remain high.

A number of issues have been highlighted in the current methods for treatment of cerebral aneurysms. One of the major issues in the treatment of aneurysms occur in wide-neck aneurysms, wherein the fundus-to neck ratio <2.0. In these cases occlusion of the aneurysm becomes extremely difficult and risky, as embolization coils do not stay in place but migrate into the parent vessel, causing blockage. A similar situation arises whereby the proximity of a neighbouring artery causes a wide-neck-type aneurysm morphology and again can be difficult to treat using embolization coils and blockage of a parent or neighbouring artery can occur. A number of techniques have been attempted to resolve this issue but all require significant technical skill and carry a significant risk. As a result of these issues, many aneurysms go untreated.

A second issue which has been highlighted is irregular shaped aneurysms. Approximately only 1 in 9 aneurysms with complex shapes can be successfully treated using coil embolization. Location of the aneurysm is also an issue which affects the long-term outcome of the aneurysm treatment. Aneurysms which are in the direct path of blood flow have a much higher recanalization rate. In these cases, coils placed into the aneurysm tend to compress with time, providing little long-term protection from re-bleeds. Due to combinations of these issues, in approximately 34% of all cerebral aneurysms treated embolization remains incomplete.

In the majority of cases outlined above, a "wait and watch" approach is adopted, wherein the patient is subject to regular magnetic resonance (MR) or computer tomography (CT) imaging to examine the growth of the aneurysm. A conservative approach may also be followed, wherein the patient's lifestyle is modified and blood pressure is kept low by pharmacological means. However, both of these approaches place the patient in considerable risk of undergoing a cerebral haemorrhage. If the aneurysm is particularly large (>7 mm) and there is a high chance of a haemorrhage then an open craniotomy will be carried out, followed by surgical clipping. However, this procedure is only possible when the location of the aneurysm allows and subjects the patient to a higher risk of morbidity or mortality. New techniques have begun to become available to the clinician for treatment of wide-neck aneurysms, including 3-dimensional coils, dual microcatheter techniques, temporary inflation of a balloon to allow coil placement and intracranial stent placement. However, these techniques often fail to successfully embolize the aneurysm, they are highly skilled procedures carried out by few clinicians and they may increase the risk of vascular injury and thrombo-embolism. These treatments remain far from ideal for the clinician.

There therefore continues to be a need for improvements in treatment of aneurysms.

SUMMARY

To address these and other problems the present teaching provides a gallium silicate glass composition as detailed in the claims as follows. Advantages methods and uses of same are also detailed in the claims.

Using standard nomenclature it will be understood that Ga is the symbol for gallium and Si the symbol for silicon and this standard nomenclature will be used within the present specification. The Ga imparts a suitable level of radio-opacity and optimises X-ray visualisation, whereas the Si acts as an important mineral in the production of collagen and may strengthen vascular walls. The molar ratio gallium to silicon plus phosphorous is desirably from 0.1 to 1.0 and the calcium to gallium ratio is desirably from 0.5 to 2. The present inventors have realised that while silicon naturally forms a stable tetrahedral structure, which is not liable to acid degradation, the addition of gallium in this composition produces an acid labile tetrahedral structure, allowing for degradation of the glass in an acidic aqueous environment. In this context the phrase tetrahedral defines a structure of molecules and polyatomic ions that have one atom in centre and four atoms at the corners of a tetrahedron. Acid labile compounds are those category of compounds that are easily broken down by acidic media or in which ions are easily liberated from that compound in acidic media. In this case the charge compensated tetrahedral structure facilitates acid lability and hence ion release from the glass. This acid labile tetrahedral structure may be charge balanced by the presence of adjacent mono-valent or di-valent ions such as calcium. The divalent ions such as calcium are advantageously employed for two reasons; to charge balance the gallium so as it can form a tetrahedral structure and to disrupt the network connectivity so as to get a sufficiently reactive glass. The presence of this acid labile tetrahedral structure infers a degree of stability to the overall glass network via increased network connectivity, allowing for slow, time dependent acid degradation and ion release.

In an exemplary arrangement the glass has a form X—$Ga_2O_3$—$SiO_2$—Y—Z where:

X is an oxide of calcium or other divalent ions such as barium, lanthanum, strontium, beryllium, magnesium, radium or zinc;

Y is an oxide of phosphorous or boron; and

Z is a halide salt such as chloride salt provided in the form of one or more of $CaCl_2$, $BaCl_2$, $SrCl_2$, $MgCl_2$, $NH_4Cl$, $ZnCl_2$, $GaCl_3$, LiCl, NaCl or KCl.

The addition of additional materials such as phosphorous into the glass structure increases glass degradability by adding additional phosphorous-oxygen bonds into the glass network, which are easily hydrolysed. In addition, the provision of $P_2O_5$ has a beneficial effect on the viscosity-temperature dependence of the glass, increasing the working temperature range which is advantageous for the manufacture and formation of the glass. However, the addition of phosphorous also allows for increased 'working time' as a result of temporary chelation of di- and tri-valent ions which are released from the glass network. In certain configurations a halide such as chlorine may be added to the glass which causes depolymerisation of the glass network, increases the glass forming potential of the composition and facilitates glass dissolution and ion exchange.

A glass composition per the present teaching may advantageously be provided in a hydrogel matrix so as to provide a therapeutic, antibacterial hydrogel. This may find particularly advantageous applications for the treatment of aneurysms and particularly for use in the treatment of cerebral aneurysms. In accordance with the present teaching the hydrogel comprises glass particles which release ions over time and are beneficial in preventing further atherosclerosis and vasospasm, aiding vasodilation and preventing infection. In such an application the provision of the divalent ions such as calcium are useful as when they are released from the glass they will also act to crosslink the alginate as occurs with gallium.

The glass may further include potassium (K) which may advantageously reduce incidences of vasospasm and increase vasodilation. Ion release into the surrounding biological fluids can be tightly controlled via composition of the glass phase.

One exemplary glass compound per the present teaching will have a form CaO—$Ga_2O_3$—$SiO_2$—$P_2O_5$—$CaCl_2$

DETAILED DESCRIPTION OF THE DRAWINGS

Figure 1A:
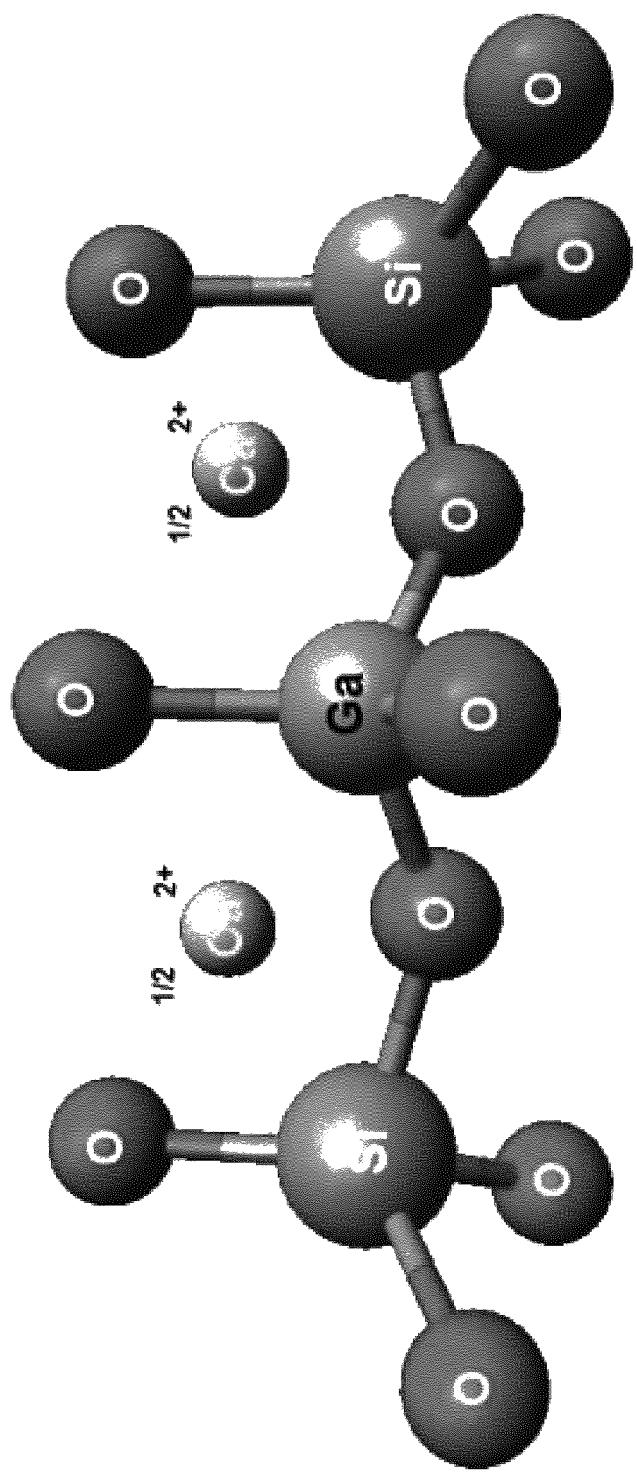
FIG. 1A shows in schematic form a structure of a glass provided in accordance with the present teaching.
Figure 1B:
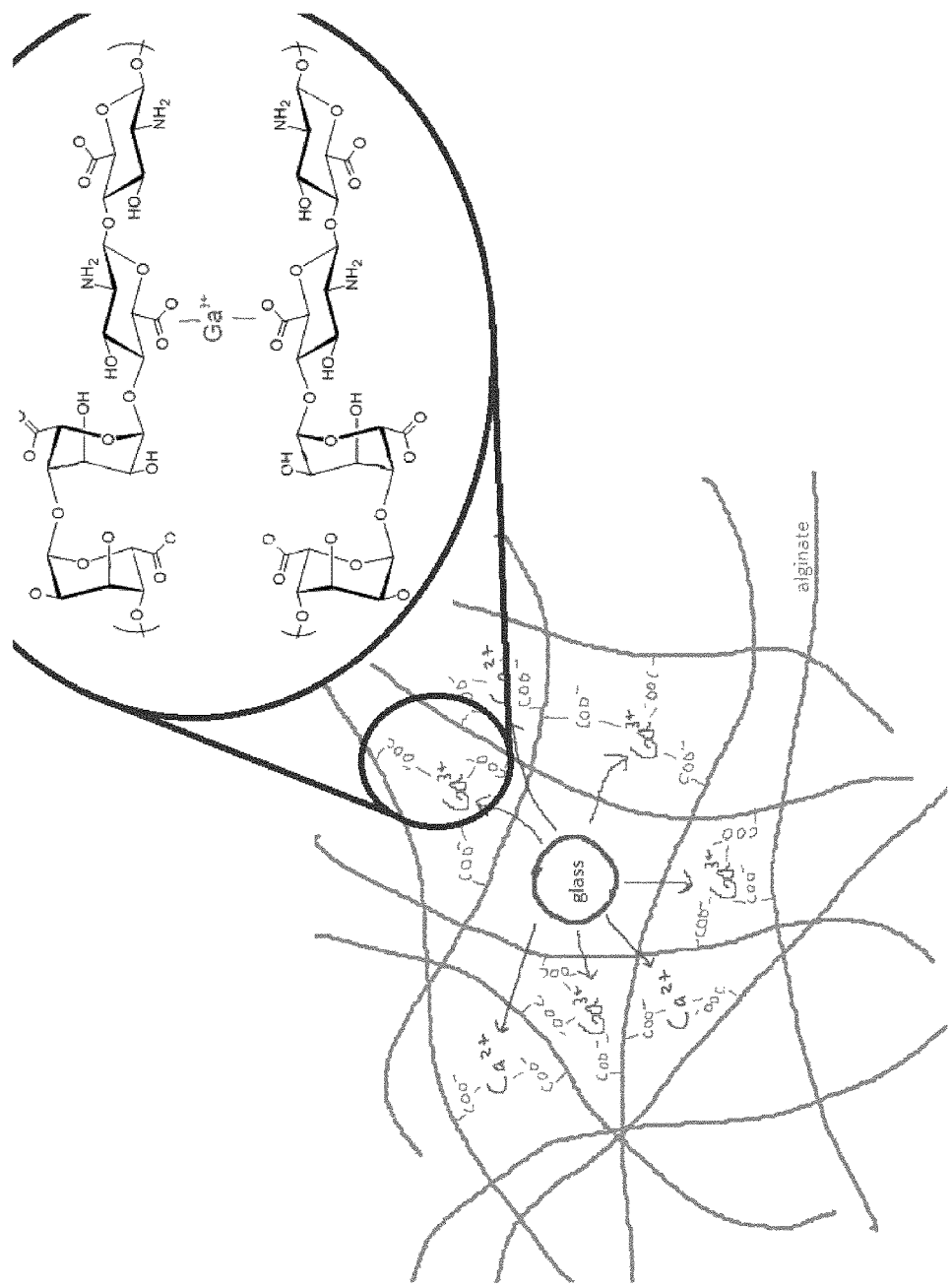
FIG. 1B shows in schematic form an alginate gel matrix incorporating a glass per FIG. 1A.

FIG. 1A shows in schematic form an exemplary glass composition CaO—$Ga_2O_3$—$SiO_2$—$P_2O_5$—$CaCl_2$ provided in accordance with the present teaching. Such a glass can be reacted with an ionically crosslinked polymer matrix, for example an alginate polymer solution such as potassium alginate, to produce a gel with controlled setting kinetics. An example of such a composition is shown in FIG. 1B where it is evident that the alginate provides a series of cross-linked threads within which the glass is embedded. The set gel produces a biocompatible, mechanically stable, flexible material, which provides controlled release of therapeutically beneficial ions. The glass composition is designed to incorporate large quantities of di- and tri-valent ions in order to fully crosslink the alginate polymer but to provide them in a stable uniform composition to allow controlled setting. This special character is provided predominantly by the inclusion of gallium into the composition which produces an acid labile tetrahedral structure.

The alginate can be provided by a polysaccharide composed of β-D-mannuronic acid (M) and α-l-guluronic acid (G), giving alginate a M/G block structure. An alginate such as this has the ability to gel when the G-blocks are cross-linked with multivalent ions. Alginates are typically described in terms of molecular weight and the G/M ratio. G-rich gels are stronger than M-rich gels, but are more brittle.

In this glass calcium could be partially or wholly replaced by other divalent ions such as barium, lanthanum, strontium, beryllium, magnesium, radium or zinc. Chlorine could equally be partially or wholly replaced by fluorine, bromine or iodine. Phosphorous could be partially or completely replaced by boron.

Advantageously, a glass of the present invention provides controlled release of metal ions in an acidic environment in order to set a polymer matrix. Controllable release rates are of critical importance for regulating the working time and setting time of the gel as well as controlling the biological response. Whilst many metals are important for physiological function, toxicity may occur in local tissue or systemically at high concentration and/or long-term exposure to certain metal ions. For example, low doses of gallium can have significant advantages such as immunosuppressive, anti-inflammatory and antineoplastic effects. However, at higher doses, gallium ions can form insoluble hydroxides and cause renal toxicity. Hence, control of release is vitally important for any implantable device which contains gallium. Similarly, too high calcium levels in the blood can cause hypercalcemia, resulting in renal or biliary stones and even arrhythmia.

The local physiological concentration of metal ions is dependent upon glass composition, metal type, application and target tissue. The composition of the glass is vital for controlled release. Only with specific compositional ranges can controlled release at physiological, and not pathological, ranges occur. For example, a highly crosslinked glass would in general prevent ion release, whilst a highly disrupted glass would release too many ions too quickly. In a preferred embodiment, a glass containing a high concentration of di- and tri-valent metal ions is used, however due to the specific composition of the glass, these ions are entrapped in a highly crosslinked glass network, which minimises ion release in a neutral pH environment, while providing acid liable bonds within the glass network which can be targeted, allowing controlled ion release, which acts to crosslink polymer chains forming a set gel.

It is undesirable to stimulate mineralisation in soft tissues and this is a major drawback of many existing glass compositions for soft tissue applications. In silica based glasses, $SiO_2$ forms the amorphous network of the glass, and the molar percentage of $SiO_2$ in the glass affects its Network Connectivity (NC). NC is the average number of bridging bonds per network forming element in the glass structure. NC determines glass properties such degradability. At an NC of 2.0 it is thought that linear silicate chains exist of infinite molar mass. As NC falls below 2.0, there is a rapid decrease in molar mass and the length of the silicate chains. At an NC above 2.0, the glass becomes a three dimensional network. For the glass to be degradable, NC must be below 2.6, or more preferably below 2.4. Glasses provided in accordance with the present teaching may, in certain aspects, be designed to be non-apatite forming, non-soluble and stable under normal physiological conditions, only releasing considerable ion release when in acidic or basic conditions, such as the acidic condition induced when forming a gel with a polymer solution.

Glasses in accordance with the present teaching may comprise of gallium oxide combined with a one or more glass former (silicon, phosphorous, germanium, boron, arsenic, antimony) and one or more components selected from a source of calcium chlorine, barium, strontium, lanthanum, tantalum, magnesium, boron, zinc or alkali metal such as lithium, sodium or potassium. Preferably these components are provided as compounds including, but not limited to $SiO_2$, $P_2O_5$, $Ga_2O_3$, $GaI_3$, $Ga_2Cl_4$, $GaF_3$, $GaP$, $GaN$, $Ga(NO_3)_3$, $Ga_2(SO_4)_3$, $GaBr_3$, $CaCl_2$, $CaO$, $CaCO_3$, $Ca(NO_3)_2$, $CaSO_4$, calcium silicates, calcium phosphates, $Na_2O$, $Na_2CO_3$, $NaNO_3$, $Na_2SO_4$, sodium silicates, sodium phosphates, $K_2O$, $K_2CO_3$, $KNO_3$, $K_2SO_4$, potassium silicates, potassium phosphates, $MgO$, $MgCO_3$, $Mg(NO_3)_2$, $MgSO_4$, magnesium silicates, magnesium phosphates, $ZnO$, $ZnCO_3$, $Zn(NO_3)_2$, $ZnSO_4$, and zinc silicates, and any such compounds that decompose to form an oxide.

Where glasses per the present teaching are referred to above as being formed from or comprising certain components, it will be appreciated that the glass is formed from these components, but that additional components may also be present within the glass network. Therefore it will be appreciated that a glass per the above description does therefore also encompass glasses having the glass compositions as described herein, where no additional components are present within the glass network i.e. glasses consisting essentially of the described components.

It will be appreciated that the exact molar percentage of the components of the glass affects the physical and biological properties of the glass. Different uses of the glass require different properties, and hence the properties of the glass may be tailored to a particular intended use by adjusting the molar percentage of each component. For example, the chemical composition of glasses can be tailored for specific applications, for example increasing apatite forming ability for orthopaedic applications by increasing Na, K, Ca, P and or Si concentration or addition or increased concentration of other elements to encourage bone forming ability or other physiological function, such as Sr, Mg, and or Zn. Additionally, calcium in the glass composition may be wholly or partially replaced by barium or lithium for increased radiopacity or replaced by magnesium, or strontium to prevent the formation of deposits in vivo or to decrease ion release or degradability. The present inventor has identified that addition of barium as a replacement for calcium within the glasses can be used to increase the radiopacity of the final gel matrix and does not inhibit the setting mechanism of the hydrogels and may results in a gel with higher compressive strength. Levels of barium released from the gel initially result in endothelial cell death but subsequent ion release encourages endothelial cell growth. This initial cytotoxic effect could be useful in inhibiting cell mediated recanalization surrounding the implant and subsequent cell growth may encourage re-endothelialisation of the implant.

In the context of improving radiopacity, iodine may also be separately tagged to the alginate backbone to increase radiopacity.

In another embodiment, a glass in accordance with the present teaching includes a source of boron, preferably as $B_2O_3$. As with $P_2O_5$, $B_2O_3$ is believed to have a beneficial effect on the viscosity-temperature dependence of the glass, increasing the working temperature range which is advantageous for the manufacture and formation of the glass. $B_2O_3$ is also believed to increase the size of the processing window between the glass transition temperature of the glass and the onset temperature for crystallisation, allowing the sintering of glass powders without crystallisation. This is advantageous as the formation of crystals in the glass generally decreases its apatite forming ability.

A glass provided in accordance with the present teaching preferably comprises a halide source such as chlorine, preferably, in the form of one or more of $CaCl_2$, $BaCl_2$, $SrCl_2$, $MgCl_2$, $NH_4Cl$, $ZnCl_2$, $GaCl_3$, $LiCl$, $NaCl$ or $KCl$. Chlorine, similarly to other halides, acts to disrupt the glass network reducing network connectivity and increasing glass disruption and dissolution rate. Chlorine may also act to chelate di- and tri-valent ions during gelation, increasing working time of the gel. Chlorine also expands the glass forming range of glasses by increasing the disruption in the glass, both due to charge and ionic size. Chlorine may also decrease the melting temperature of the glass, facilitating manufacture.

Depending upon its intended use, the glass may be provided in particulate form, as 3D structure or as a solid such as a disk or monolith. In particular, the glass can be provided in any required shape or form, for example as a pellet, sheet, disk, foam, etc. In particulate form, the preferred particle size depends upon the application of the glass in question, as well as the reactivity required, however preferred ranges of particle sizes are less than 1200 microns, preferably between 1 and 200 microns, more preferably 2 to 50 microns. The range of particle size required depends upon the application and the reactivity of the glass required. If mixed with a polymer for the purposes of crosslinking, the glass may be provided in large particulate form (>10 micron) for slow or reduced reactivity or in a fine particulate form (<10 micron) for more rapid or more complete reactivity. The glass powder may be sintered to create coatings or to form a porous solid for use as a scaffold. In addition, the glass may be in the form of granules. The glass may be incorporated into a non-degradable or degradable polymer scaffold for use in various medical applications. This polymer/glass material may be in a gelling form or as a gelled or set scaffold, for adhesive, embolization, filler or tissue engineering applications or to deliver some therapeutic value.

The glass is preferably provided as a melt-derived glass but may also be provided as a sol-gel derived glass, produced by known technology. The glass can further be annealed or sintered using known technology. The melt-derived glass is preferably prepared by mixing and blending grains of the appropriate carbonates or oxides, melting and homogenising the mixture at temperatures of approximately 1250° C. to 1550° C. The mixture is then cooled, preferably by pouring of the molten mixture into a suitable liquid such as deionised water, to produce a glass frit.

The glass chemical composition and form will depend upon the application. The glasses can be used in particulate form, as monoliths, 3D porous scaffolds, fibres and/or coatings incorporated into or onto implanted materials, tissue regeneration constructs and wound healing devices, such as tissue engineering scaffolds, sutures, prosthetic implants, polymer matrixes, fibrin gels, hydrogels, plasters, wound dressings, creams, shampoo and the like. The glass compositions can also be used in devices used for in vitro and ex vitro cell culture. Furthermore, the glasses could be used elicit certain cell responses in vitro prior to therapeutic use of cells in vivo.

While glass has been used as a biomaterial since the development of the now commercially available product Bioglass™ in the 1960s, the use of these materials has primarily focused on their application in the area of bone repair and bone regeneration. It is also known to use a Glass Polyalkenoate Cements (GPCs) of the form sometimes referred to as Wilson's glass ionomer cement formulations as dental cements. Known GPCs are formed using aluminium (Al) which has reported neurotoxicity affects. Other known attempts to provide a bioactive glass, and by this term we mean capable of eliciting a positive biological response, have included iron (Fe) and zinc (Zn) based glasses which also have toxicity and reactivity issues.

These known glasses are typically composed of $SiO_2$, $Na_2O$, $CaO$ and $P_2O_5$ in specific proportions and differ from traditional non bioactive glasses in the low amount of silica (less than 60 mol. %). To date however there has been resistance in the widespread use of these materials based on these toxicity and reactivity issues.

In contrast to these known glasses, the present inventors provide a Ga based glass that has reduced neurotoxicity relative to previous known compositions and has realised that these type of glasses can have application in the various treatments, particularly in the treatment of aneurysm repair. Whereas traditional GPCs mix an aluminium glass with a poly(alkenoaic acid), typically poly(acrylic acid), the present teaching provides Ga as a substitute for the Al in the glass network and combines that with a potassium alginate. It will be appreciated that the alginate is not acidic and so an activator (GDL) is required to initiate ion release from the glass. GDL is a lactone that hydrolyses in water to form a gluconic acid, its role in the hydrogel is to acidify the solution. This in turn encourages release of multivalent ions from the glass, allowing them to cross-link with the alginate G-blocks. The gelation of the hydrogel can be controlled by both the composition of the glass phase and the ratio of constituent components of the gel. The alginate does comprise carboxylic side groups which are crosslinked by the released ions from the glass. However, in another contrast to known GPCs, a glass alginate in accordance with the present teaching has a higher water content and the overall composite is a lot less stiff than the known GPCs which it will be appreciated are intended to be stiff considering their application as a dental glue.

While a sodium alginate could be used within the context of the present teaching, potassium alginate is preferred as potassium is not as deleterious to the arteries, as sodium may be. Potassium may also have a role in vasodilation, vascular relaxation and in preventing vasospasm, which can be an issue when treating vasculature. In addition to this, the potassium salt of alginic acid is easier to dissolve in aqueous solutions and we can acquire higher alginate concentrations in solution, providing a larger viscosity working range.

It will be appreciated that Gallium is not redox-active under physiological conditions and may serve to reduce hydroxyl radical formation in vivo. Glasses containing gallium are thought to be isostructural with those containing aluminium and in this respect, it is believed that gallium forms a tetrahedra in silica glasses similar to aluminium in aluminosilicate glasses, assuming that there is sufficient alkali or alkaline earth oxides to charge balance the gallium tetrahedral. The tetrahedral form provides the glass with a highly crosslinked network (high network connectivity) while still providing the glass with a high ion content. These tetrahedra are important to the acid degradability of the glass and are the only way to provide a slow ion releasing glass, while providing a high enough ion content for full cross-linking of the alginate.

Similarly to the formation of a GPC when mixed, these glasses, react in an acidic environment releasing trivalent and divalent ions into the aqueous environment and forming a silica gel on their surface and over time. This mechanism can be used to crosslink hydrogels, in particular those which contain carboxylic side groups. Glass particles continue to release ions into the aqueous environment over time, replenishing any ions released from the hydrogel into the surrounding fluids and tissues. These gels form a composite of embedded partially reacted glass in the hydrogel matrix as is evident from an inspection of FIG. 1B. Gallium (Ga) in the silicate structure of these glasses may be in six-fold coordination with oxygen (network modifier) or in four-fold coordination (network former). The Ga may substitute for silicon in the basic $SiO_4$ unit and acquire a four-fold coordination due to its similar ionic radius to silicon. However, this results in an extra negative charge on the $GaO_4$ tetrahedron. This negative charge must be balanced by positively charged network modifying cations, such as $Ca^{2+}$ if the four fold coordination of gallium is to be maintained. This four-fold structure allows the glass structure to contain a large quantity of di- or tri-valent ions without crystallisation or becoming excessively reactive.

In a pure silica glass the network is covalently bonded, electrically neutral and stable in structure, which renders it impervious to acid attack. The introduction of network-modifying cations and gallium ions renders the glass structure vulnerable to acid attack by increasing the polarization of oxygen ions. Acid attack of the basic calcium rich sites in the glass results in rupture of the gallium silicate network at gallium sites and degradation of the glass structure. The ability of a glass to form a gel with an ionically crosslinkable polymer is governed by the $SiO_2/Ga_2O_3$ ratio which represents the acid-base balance in these glasses. If this ratio is too high then the glass will be too stable and will not release ions to form a gel, if the ratio is too low then the gelation occurs too rapidly and the gel will not be cohesive.

The present inventors have realised that poly(acrylic acid) hydrogels which are traditionally used in GPCs are unsuitable for arterial applications due to their high stiffness. A number of replacement polymers were evaluated and an alginate was determined to be the most suitable for arterial applications. Accordingly, a small particle size calcium gallium silicate glass, containing some chloride (described above) was produced and reacted with an alginate solution to produce a flexible hydrogel composite which has a controlled setting rheology and results indicate that it is suitable for treatment of cerebral aneurysms.

Accordingly the present teaching provides new glass compositions comprising gallium oxides. These novel compositions can be reacted with an alginate solution to produce a suitably fluid composition. This composition sets within 35 minutes to produce a cohesive flexible mass. Tests indicate stability of this material in an aqueous environment with no significant change in mechanical properties over a period of at least three days, which is a result of the controlled release of ions from the glass phase. Calcium chloride crosslinked alginates form gels rapidly (within seconds) and their strength deteriorates rapidly in saline solutions.

Advantageously this novel material has controlled and adjustable rheological properties and the setting time of the setting material may similarly be controlled. The control of the setting time is influenced by one or more of glass composition, alginate chain length, alginate concentration, glass particle size, glass concentration and GDL concentration.

For example, alginate molecular weight, chemical composition and concentration affect the usability of the composition as an aneurysm filler. Scientific studies by the present inventor has shown that a 4.5% alginate concentration of a 60 kDa alginate has an acceptable strength and working time, however concentrations in the range 2.4% to 6% can be advantageously employed depending on the specifics of the application. While a 4.5% and 6% alginate concentration have the correct hardening time and the 2.4% and 4.5% alginate concentration are the only injectable concentrations, it is clear that the 4.5% alginate concentration meets all the requirements, but it will be appreciated that it is not intended to limit the present teaching to such a specific value. Similar analysis of a 700 kDa alginate demonstrated that a 4.5% alginate concentration was the only concentration the met each of the requirements. Based on flexibility and capacity to be sterilised at lower gamma irradiation levels concentration 4.5% of the 700 kDa can be considered a preferred alginate as it demonstrates advantageous molecular weights, chemical composition and alginate concentration for the intended application of intracranial aneurysm treatment. In this regard however it will be appreciated that ultimate viscosity and strength of the alginates may be caused by a combination of factors including molecular weight and chemical composition. For example, it is observed that a 180 kDa alginate has a reduced viscosity when compared to a 60 kDa alginate and this may be caused by the G/M ratio of the alginates, as high-M content alginates are weaker and more flexible compared to that of a high-G content alginate. Similarly a reduced viscosity of the same 180 kDa alginate when compared to a 700 kDa alginate may be due to the molecular weight. The molecular weight and G/M ratio also affects the working and hardening time of the hydrogel. As there is a reduced number of G-blocks available in the hydrogel, it takes the gel longer to bind with multivalent ions. In this way it will be appreciated that alginate viscosity affects the injectability of the hydrogel. Alginates with a viscosity between 2000 and 9000 mPas can inject well through a hydrogel and will likely remain within the aneurysm in a blood flow environment.

It will be appreciated that in such complex mechanisms there are a number of parameters that may be modified to control working and setting time. Acid washing of the gallium silicate glass has been found to advantageously increase wettability and allows better mixing with an alginate solution. The resultant gel has a longer working and setting time and forms a gel with a higher compressive strength. The longer working and setting time allows for an increased glass content, which in turn increases the hydrogel's compressive strength. Acid washing of the glass, for example by placing a glass sample into a liquid volume of 2 vol. % acetic acid for repeated periods of about an hour, qualitatively resulted in improved mixability and homogeneity of the glass samples and has an effect on the particle size, surface topography, pore size, surface ion content and surface network connectivity, all of which contribute to the working and setting time of the resultant hydrogel. The increased compressive strength which can be observed subsequent an acid washing is likely an effect of the reduced divalent ion content of the surface and increased trivalent ion content, resulting in more complete crosslinking of the alginate hydrogel.

It will be appreciated therefore that there are a number of mechanism by which the ultimate properties of the glass may be varied. By providing a glass composition that has tuneable properties, combined with its low toxicity, high biocompatibility and intrinsic long-term radiopacity, the present inventors have provided a composition that may be advantageously employed in correction of defects that are found in a variety of vascular applications. A glass and polymer composition per the present teaching may find particular application in the treatment of defects in arterial vascular networks, such as use in endovascular aneurysm filling applications, as well as in the treatment of AVM and other neurovascular problems. The material's potential therapeutic benefits, in decreasing vasospasm and encouraging vasodilation, as well as its likely antibacterial nature are seen as secondary (though not insignificant) benefits. As was outlined above in the background section, current approaches suffer from either poor biocompatibility or poor control of setting and rheological properties and all of the current technology suffers from poor tissue adhesion/apposition. A composition provided in accordance with the present teaching addresses all of these issues and can provide a better alternative to the market and to the end-user.

Experimental Results
1.1 Glass Synthesis

Four glass formulations were synthesized. Glasses OC200, OC201, OC202, and OC203. OC200 contains only silica, alumina, calcium, phosphorous pentoxide and calcium chloride, while OC201, OC202, and OC203 contain increasing quantities of gallium trioxide at the expense of alumina. Table 1 illustrates the glass compositions, expressed as mole fractions, examined in this work.

TABLE 1

Glass series (mole fraction).

| Glass: | Oxides (mole fraction): | | | | | |
|---|---|---|---|---|---|---|
| | $SiO_2$: | $Al_2O_3$: | $Ga_2O_3$: | CaO: | $P_2O_5$: | $CaCl_2$: |
| OC200 | 0.33 | 0.18 | 0.00 | 0.23 | 0.11 | 0.15 |
| OC201 | 0.33 | 0.12 | 0.06 | 0.23 | 0.11 | 0.15 |
| OC202 | 0.33 | 0.06 | 0.12 | 0.23 | 0.11 | 0.15 |
| OC203 | 0.33 | 0.00 | 0.18 | 0.23 | 0.11 | 0.15 |

Glasses were prepared by weighing out appropriate amounts of analytical grade reagents (Sigma-Aldrich, Dublin, Ireland), as outlined in Table 2 and mixed in a rotor for 10 minutes. Compositions were subsequently fired (1480° C., 1 h) in 10% Rhodium/Platinum crucibles and shock quenched into water. The resulting frit was dried (100° C., 1 h) before being ground using a vibratory mill to <63 μm. The glass powder was then further ground in methanol in an attrition mill using 1 mm alumina media. Methanol was subsequently evaporated to retrieve the final glass powder.

TABLE 2

Glass series (grams).

| Glass: | Oxides (g): | | | | | |
|---|---|---|---|---|---|---|
| | $SiO_2$: | $Al_2O_3$: | $Ga_2O_3$: | $CaCO_3$: | $Ca(H_2PO_4)_2 \cdot H_2O$: | $CaCl_2$: |
| OC200 | 4.95 | 4.59 | 0.00 | 3.00 | 6.93 | 4.15 |
| OC201 | 4.95 | 3.06 | 2.81 | 3.00 | 6.93 | 4.15 |
| OC202 | 4.95 | 1.53 | 5.62 | 3.00 | 6.93 | 4.15 |
| OC203 | 4.95 | 0.000 | 8.44 | 3.00 | 6.93 | 4.15 |

1.2 X-ray Diffraction

Powdered samples of each glass were adhered to a glass slide and analysed using Cu Kα1 radiation emitted from a Brüker D8 Advance X-ray diffraction unit (Brüker, Billerica, Mass., USA). A generator voltage of 40 kV and a tube current of 35 mA were employed. Diffractograms were collected in the range of $10°<2\theta<80°$, at a scan step size of 0.1° and a step time of 5.0 s. Diffractograms were analysed and any crystalline phases present were identified using JCPDS (Joint Committee for Powder Diffraction Studies) standard diffraction patterns.

1.3 Particle Size Analysis

Particle size analysis was carried out using a Malvern Mastersizer® 3000 (632.8 nm He—Ne laser) fluid module particle size analyser (Malvern, UK). Particles were pre-sonicated for 15 seconds and analysed in a 100% Methanol dispersion medium. Laser obscuration was in the range 2.50-3.50% and particles were analysed in the range 0.010 μm to 3500.000 μm.

1.4 Network Connectivity Calculations

The network connectivity (NC) of the glasses was calculated with Equation 1 using the molar compositions of the glass.

$$NC = \frac{\text{No. } BOs - \text{No. } NBOs}{\text{Total No. Bridging Species}} \quad \text{Equation 1}$$

Where:
BO=Bridging Oxygens and
NBO=Non-Bridging Oxygens 1.5 Differential Thermal Analysis A combined differential thermal analyser-thermal gravimetric analyser (DTA-TGA, Stanton Redcroft STA 1640, Rheometric Scientific, Epsom, England) was used to measure the glass transition temperature (Tg) of each glass. A heating rate of 10° C. min-1 (up to 900° C.) was used. Materials were tested in an air atmosphere with a blank matched platinum crucible used as a reference.

1.6 Pycnometery

Density of each glass was determined using a Micromeritics helium pycnometer (Micromeritics Instrument Corp., Norcross, Ga., USA). 3.0-5.0 g of powder glass was analysed in a 12 cc chamber using a blank chamber as a reference. An average of 25 runs was used to determine the average density of each glass.

1.7 Magic Angle Spinning Nuclear Magnetic Resonance

Powdered samples of each glass were examined by $^{29}$Si MAS-NMR and $^{27}$Al MAS-NMR. The $^{29}$Si MAS-NMR measurements were conducted at a resonance frequency of 71.5 MHz using a 600 MHz Avance III Bruker NMR spectrometer (Brüker, Billerica, Mass., USA). The spinning rate of the samples at the magic angle was 7 kHz for $^{29}$Si. The recycle time was 1.0 min. The reference material used to measure the chemical shift was tetramethylsilane. The $^{27}$Al MAS-NMR measurements were conducted at a resonance frequency of 39.1 MHz. The spinning rate of the samples at the magic angle was 7 kHz for $^{27}$Al. The recycle time was 1.0 min. The reference material used to measure the chemical shift was $Al(NO_3)_3$. $^{71}$Ga MAS-NMR was carried out at a at resonance frequency of 183 MHz, a spinning rate of 10 kHz and a recycle time of 1.0 min, using $Ga(NO_3)_3$ as a reference standard for chemical shifts.

1.8 Composite Hydrogel Preparation
1.8.1 Purification and Sterilisation of Potassium Alginate Purification of crude sodium alginate (Sigma Aldrich, Wicklow, Ireland) was carried out in a similar fashion to published procedures with the aim of removing protein and endotoxin contamination (Dusseault et al., 2006)(Jork et al., 2000)(Zimmermann et al., 1992)(Klöck et al., 1994). During this process sodium alginate was purified by defined processes to remove any pyrogens and the sodium alginate was precipitated as potassium alginate using a potassium hydroxide solution and finally dried using lyophilisation.

1.8.2 Production of Composite Hydrogel Samples

A 2 wt. % potassium alginate was produced by mixing dry, sterile, purified potassium alginate with sterile filtered (<0.22 μm) purified water. A 9.2 wt. % glass solution was produced by sterilising OC203 glass under UV light for 15 minutes followed by sterile filtered purified water and agitating for 30 minutes. Hydrogel samples were then produced by mixing 600 μl of glass solutions with 0.05 g of UV sterilised glucono-δ-lactone (GDL) for 10 seconds, followed by mixing with 600 μl of alginate solution for a further 60 seconds.

1.9 Working and Setting Time Determination

To test for working and setting time, the composition is mixed for 1 minute before being placed in a stainless steel mould (10 mm ø, 5 mm h) sitting on a large steel block which has been pre-heated to 37° C. The hydrogel is then indented vertically using a 20 g weight with a 6 mm diameter indenter The working time is defined as the earliest time that the gel can support its own weight (remain in the mould when lifted) when allowed to set at 37° C. in a steel mould of 10 mm diameter and 5 mm height. The setting time is defined as the time at which the mark formed by the indenter after 10 seconds does not recover within one minute following indentation.

1.10 Mechanical Testing

Five samples (n=5) were produced for compression testing by mixing samples for 1 minute before placing into moulds (ø 9.00 mm, height 15.00 mm). Samples were covered with acetate sheet and allowed to set for 60 minutes before being placed into 20 ml of Dulbecco's modified eagle medium containing 1 vol. % penicillin streptomycin. Samples were tested using a 50 kN Zwick BT1-FR005TN test machine fitted with a 500N load cell and parallel plate platens. Samples were loaded at 2 mm/min to failure and data was recorded using TestXpert software (v.11.02) (Zwick, Ulm, Germany). Peak stress and corresponding strain at failure was recorded and elastic modulus prior to failure was determined (c.30-50% strain).

1.11 Elution MTT Assay

MTT Elution Assays were carried out using Bovine aortic smooth muscle cells (BASMCs) and bovine aortic endothelial cells (BAECs) as per ISO 10993-5, briefly described here. A composite hydrogel sample was produced (as described in section 1.8.2) and set in cylindrical PTFE moulds (Ø15 mm, height: 1 mm). Samples were left to set for 1 h before being placed in 2.75 ml of DMEM cell culture media (as per ISO10993-5) supplemented with 10 vol. % foetal calf serum and 1 vol. % penicillin-streptomycin (Sigma Aldrich, Wicklow, Ireland) at the bottom of 24 well plates. Samples were incubated for 24 h and 48 h (37° C., 5% $CO_2$. Elution media was gently removed and filtered through a 0.22 μm sterile filter.

BASMCs and BAECs were grown up using appropriate media (3≤p≤6). Cells were seeded at 40,000 cells per 100 μl of media in 96 well plates and incubated until they formed a sub-confluent monolayer (37° C., 5% $CO_2$). Media was then aspirated off and cells were placed in varying concentrations of elution media (0, 20, 40, 60, 80, 100 vol. %) and incubated for 24 h. MTT solution was produced by dissolving 50 mg of Thiazolyl Blue Tetrazolium Bromide in 10 ml of sterile PBS and was filtering through a 0.22 μm sterile filter. Following incubation, elution media was aspirated off, cells were washed with 100 μl of PBS ($Ca^{2+}$, $Mg^{2+}$ free), 100 μl MTT solution was placed into each well and incubated 5 hours (37° C., 5% $CO_2$). The MTT solution was then aspirated off, 100 μl of DMSO was added to each well, plates were shaken for 15 seconds and incubated at room temperature for 10 minutes. Optical densities were recorded at 540 nm with a reference wavelength at 630 nm. Cell viabilities were calculated as a percentage of untreated control cells using the equation below:

$$\text{Cell Viability (\%)} = \frac{\text{Absorbance}_{540\,nm} \text{ of treated cells}}{\text{Absorbance}_{540\,nm} \text{ of untreated cells}} \times 100 \quad \text{(Equation 2)}$$

1.12 Platelet Adhesion Analysis

Fresh bovine blood was acquired at slaughter in a 3 parts 3.8 wt. % trisodium citrate solution to 20 parts blood. Blood was centrifuged at 200 g for 20 minutes at 22° C. and a platelet rich plasma (PRP) was collected from the supernatant. Half the PRP was centrifuged at a g force of 1000 for 15 min to obtain the platelet poor plasma (PPP) from the supernatant. A platelet count was carried out from the PRP using a hemocytometer and diluted to $0.35 \times 10^8$ platelets/ml with PPP. 0.271 mg of Quinacrine mustard dihydrochloride (mepacrine) (10 μmol/L) was added to 50 ml of the platelet suspension and allowed to sit in the dark for 30 minutes at 37° C. Samples (gels and Ti6Al4V controls) were placed at the base of 6 well plates and 2 ml of platelet solutions were added to each well, ensuring that samples were fully immersed. Samples were incubated in the platelet containing solutions under static condition for 60 minutes at 37° C., 5% $CO_2$ and rinsed twice with PBS in order to remove the platelets which were not attached to the material surface. Adhered platelets were fixed by immersing samples in 2% and 5% glutaraldehyde solutions for 2 h each. Environmental scanning electron microscopy was carried out using a Carl Zeiss (Jena, Germany) EVO LS 15 scanning electron microscope, at a high relative humidity by incorporating a Deben (Suffolk, UK) cold sample stage. Secondary electron images were obtained of the surface of gels and controls. Fluorescence microscopy was carried out on an Olympus BX51 (Tokyo, Japan) at an excitation wavelength of 488 nm and captured using CellF software (Olympus).

1.13 Statistical Analysis

One way analysis of variance (ANOVA) was performed to determine significant affects across groups and comparison of means was performed using the post hoc Bonferroni test. Differences between groups was deemed significant when p≤05. All statistical analysis was carried out using Excel 2010 (Microsoft Corporations, Redmond, Wash.).

Results

Figure 2:
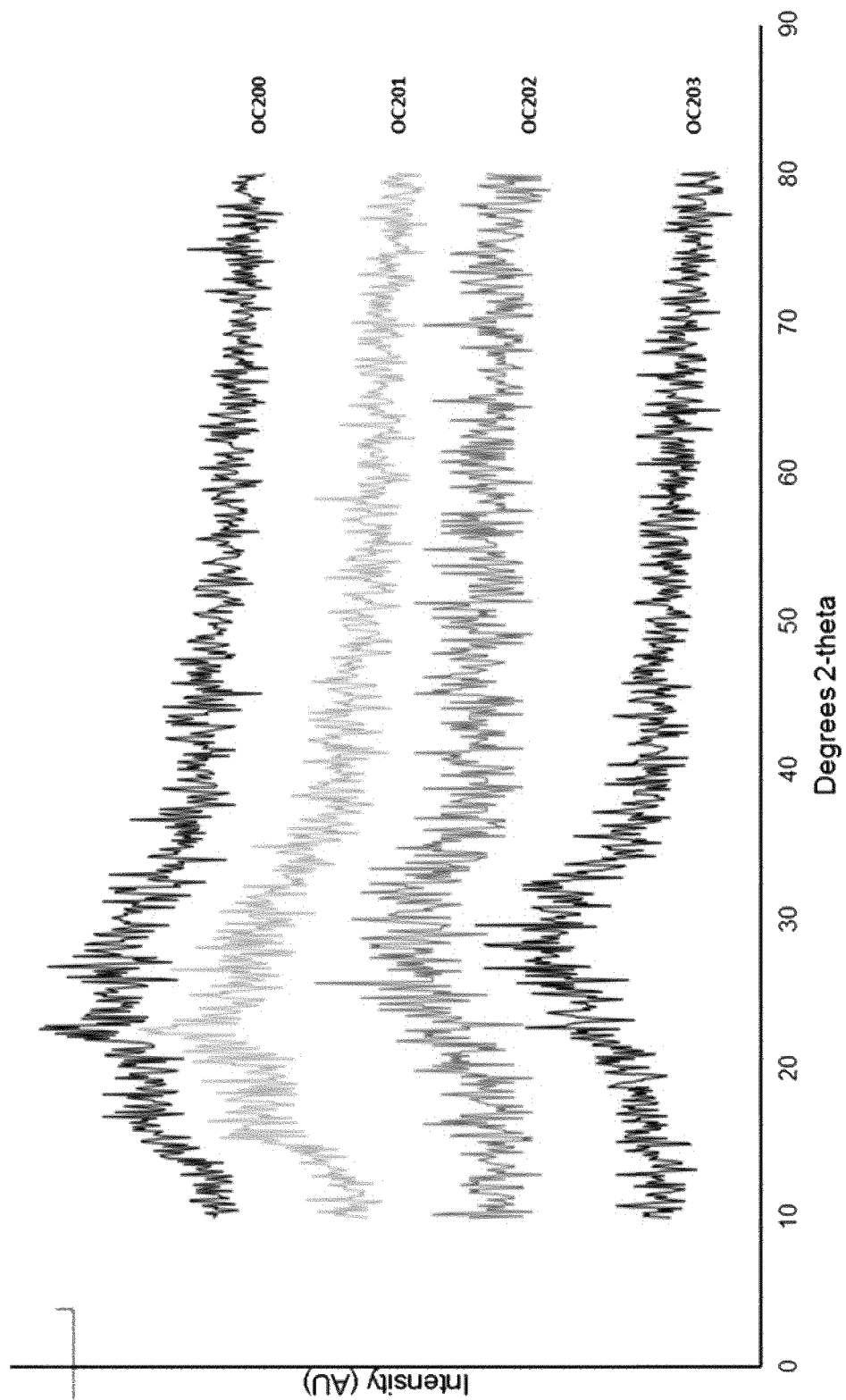
FIG. 2 provides results of X-ray diffraction of four glass compositions.
Figure 3:
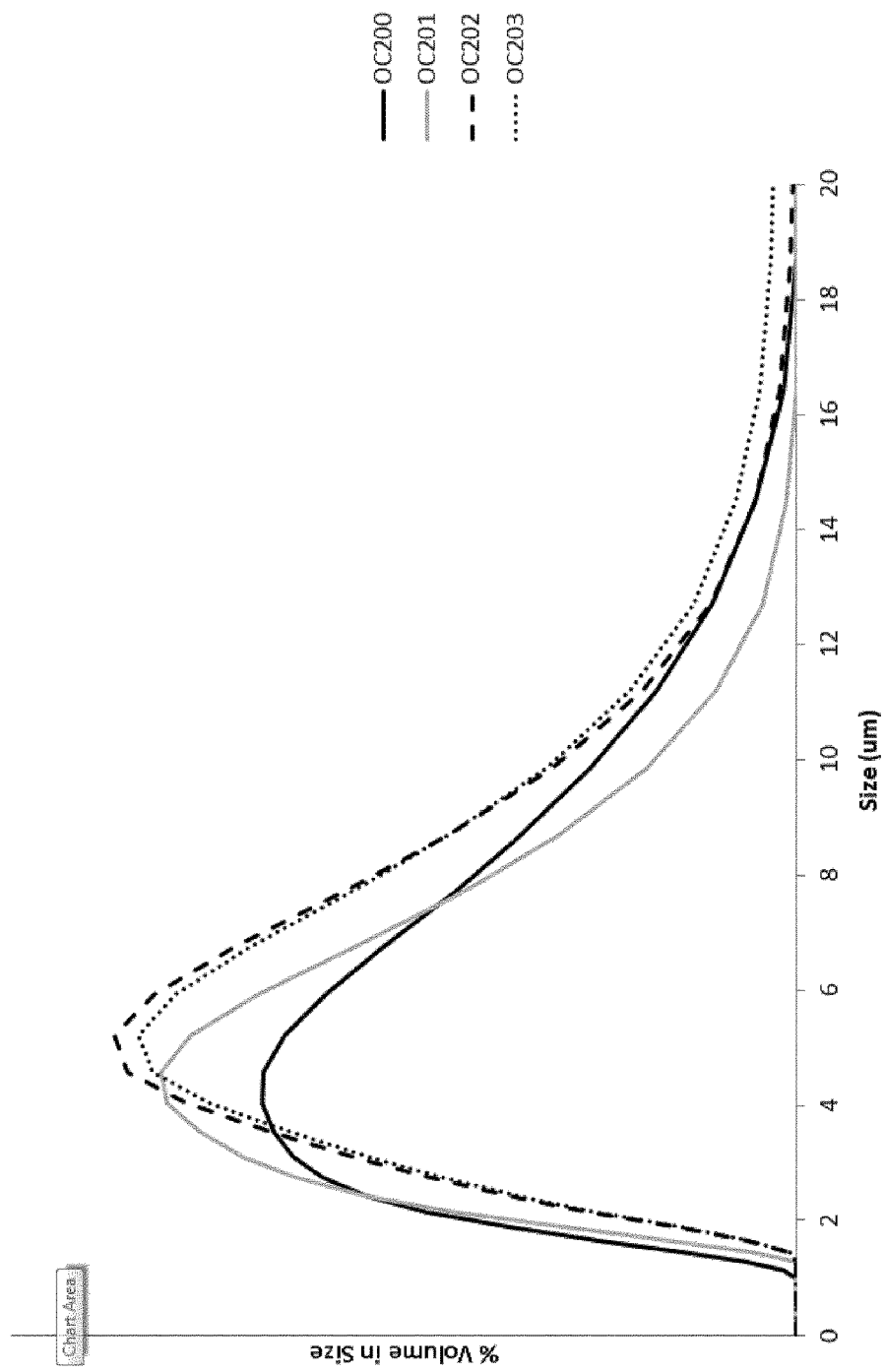
FIG. 3 shows a graph outlining particle size analysis of four glass compositions.

FIG. 2 shows how all four materials that were tested exhibit similar responses to X ray diffraction indicating that they are all amorphous in nature and there are no crystalline species evident. FIG. 3 shows that the particle size of all glasses, as determined using laser diffraction, appear relatively similar, the majority of particles in the range 1-20 μm, though OC200 and OC201 have a larger volume of fines and OC201 has a smaller volume of >10 μm particles.

Network connectivity calculations of 3.06, as demonstrated by Table 3 below, assumes that both aluminium and gallium act as network formers, forming tetrahedra by charge compensation from local calcium ions. However if this is not the case then a NC of 2.48 would result

TABLE 3

Network Connectivity calculations of glass series based on formulation

| Glass: | Oxides (mole fraction): | | | | | | NC*: | NC†: |
|---|---|---|---|---|---|---|---|---|
| | $SiO_2$: | $Al_2O_3$: | $Ga_2O_3$: | CaO: | $P_2O_5$: | $CaCl_2$: | | |
| OC200 | 0.33 | 0.18 | 0.00 | 0.23 | 0.11 | 0.15 | 3.06 | 2.48 |
| OC201 | 0.33 | 0.12 | 0.06 | 0.23 | 0.11 | 0.15 | 3.06 | 2.48 |
| OC202 | 0.33 | 0.06 | 0.12 | 0.23 | 0.11 | 0.15 | 3.06 | 2.48 |
| OC203 | 0.33 | 0.00 | 0.18 | 0.23 | 0.11 | 0.15 | 3.06 | 2.48 |

*Network Connectivity assuming gallium acts as a network former and therefore is provided in a tetrahedral arrangement.
†Network Connectivity assuming gallium acts as a network modifier and therefore acts to disrupt the network by forming trivalent species.

Figure 4:
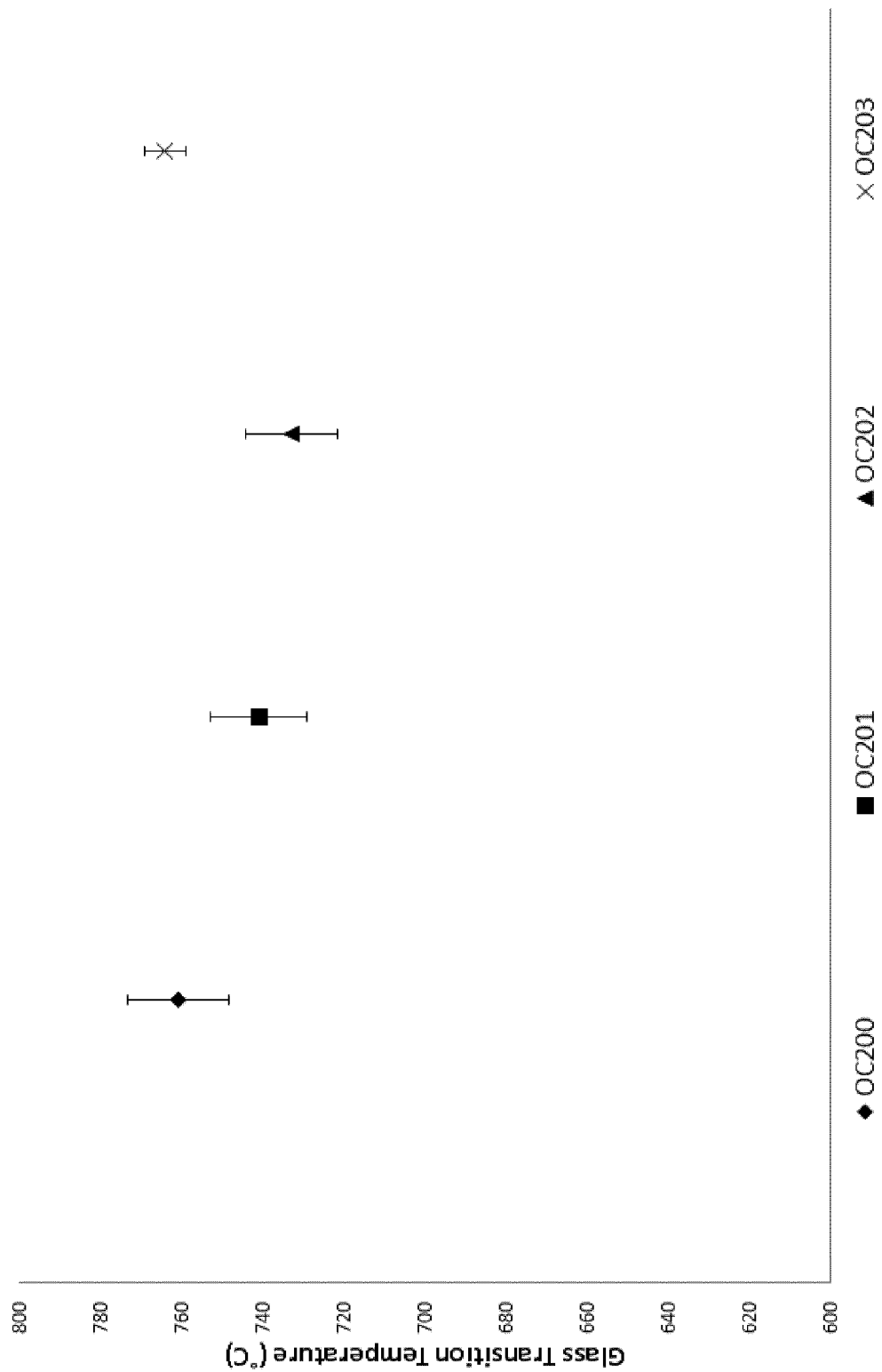
FIG. 4 is a graph showing glass transition temperature of four glass compositions.

It can be seen from FIG. 4 that the glass transition temperature does not change significantly when aluminium is replaced by gallium, indicating that the glass structural network is similar in both cases.

Figure 5:
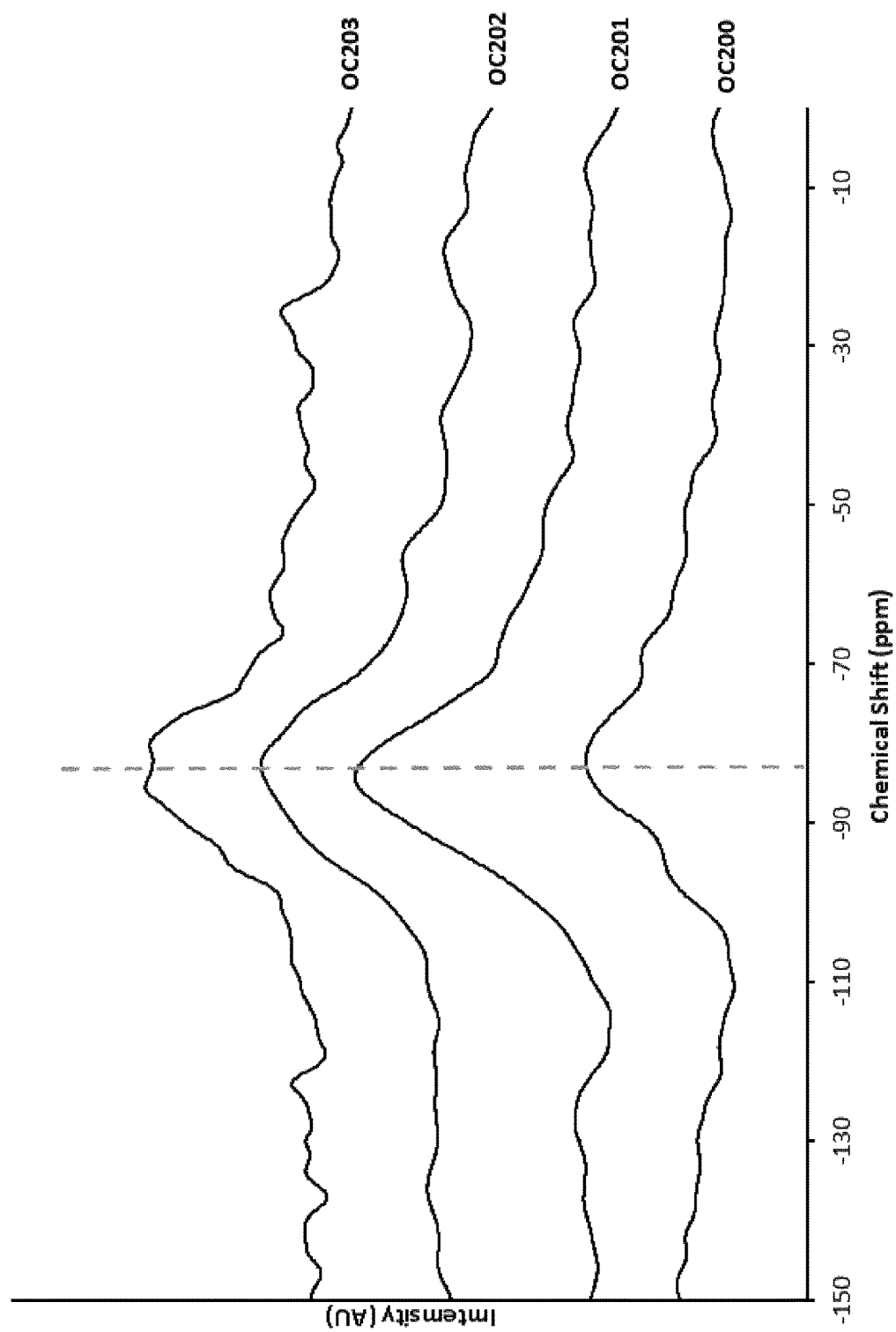
FIG. 5 is a graph showing $^{29}$Si Magic Angle Spinning—Nuclear Magnetic Resonance Spectroscopy for four glass compositions.

As can be observed from FIG. 5, $^{29}$Si MAS-NMR data is similar for all glass samples. This confirms previous thermal data that the structural network is similarly coordinated regardless of the Al/Ga ratio. The broad peak centred around −80 ppm is as would be expected for a Q2/Q3 structured silicon, though the peak cannot accurately be assigned to a specific structural unit since it is located within the chemical shift range of both Q2 and Q3 structures. In addition to this, due to the disordered nature of glass it is likely that a number of different coordination states exist for silicon within the glass network.

Figure 6:
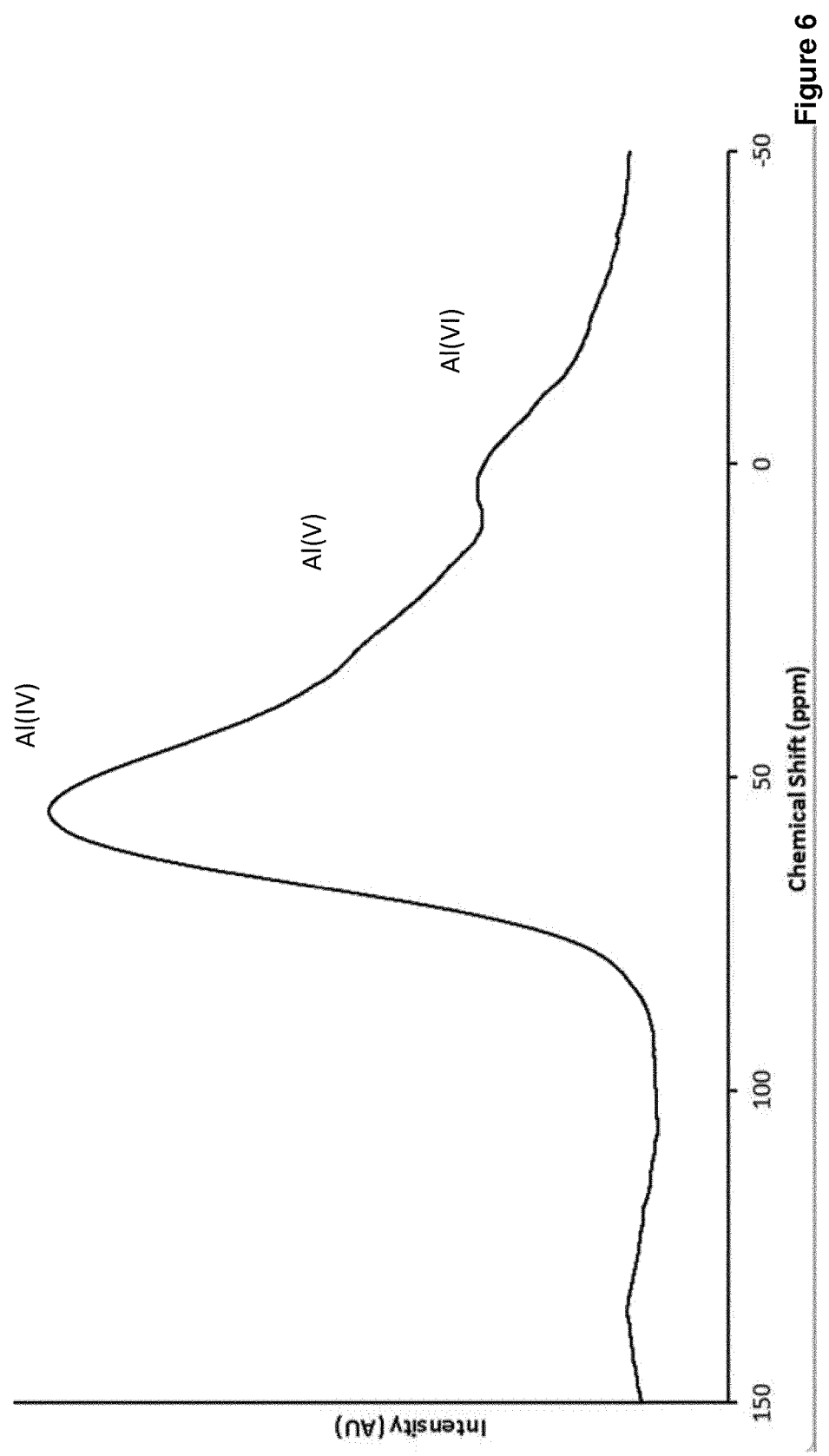
FIG. 6 is a graph showing $^{27}$Al Magic Angle Spinning—Nuclear Magnetic Resonance Spectroscopy of a known glass from which information regarding a glass provided in accordance with the present teaching may be inferred.

Examination of FIG. 6 shows the $^{27}$Al MAS-NMR spectra for OC200. There are possibly three coordination systems for Al in Glasses OC200, according to the NMR spectrum. The first one is tetrahedrally coordinated aluminum site (Al(IV)), which shows a strong peak around 55.4 ppm. There is also an octahedrally coordinated aluminium site (Al(VI)) displaying a small peak at approximately −5 ppm and a pentahedrally coordinated aluminium site (Al(V)) at 25 ppm. The peak at approximately 120 is a side band.

Figure 7:
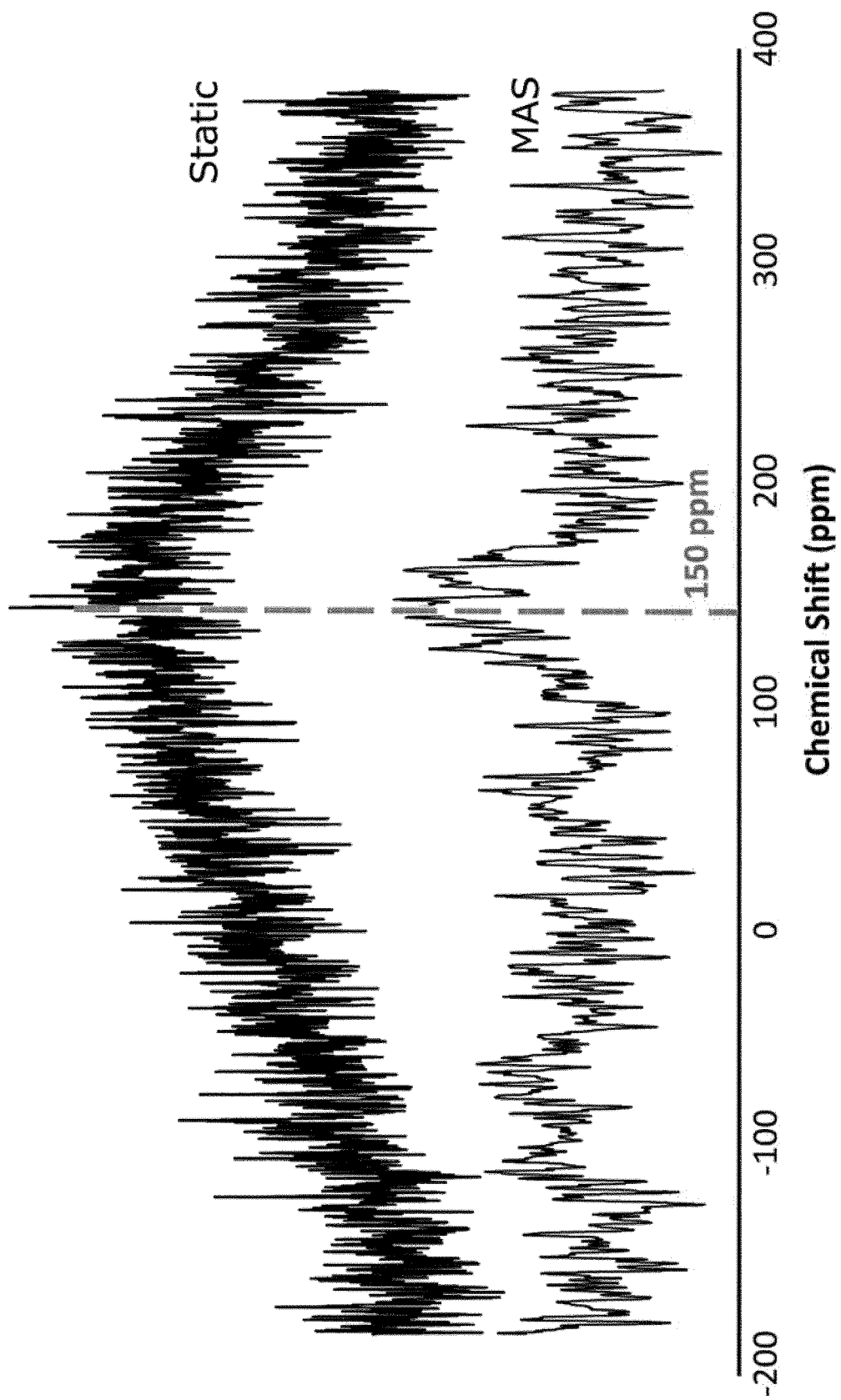
FIG. 7 is a graph of data resultant from Nuclear Magnetic Resonance Spectroscopy of a novel glass formulation per the OC203 formulation of Table 1 showing $^{71}$Ga Magic Angle Spinning.

Combining the data from FIG. 5 and FIG. 6 allows us to infer that the gallium ion is most likely coordinated in a similar manner to the aluminium ion, that is that it similarly contains a majority of tetrahedrally coordinated gallium ions (Tetrahedral:Pentahedral:Octahedral=16:3:2). As there is no lower coordination state than Ga(IV), an increased concentration of either Ga(V) or Ga(VI) would result in a decreased glass connectivity and a resultant decrease in glass transition temperature (FIG. 4) as well as a shift in the broad $^{29}$Si-NMR peak to a lower ppm. Additionally, though noise-to-signal ratio is high, FIG. 7 shows both the static and magic angle spinning $^{71}$Ga-NMR spectra for OC203, which, in both cases exhibits a peak at 150 ppm, indicating a predominantly tetrahedral coordination.

Figure 8:
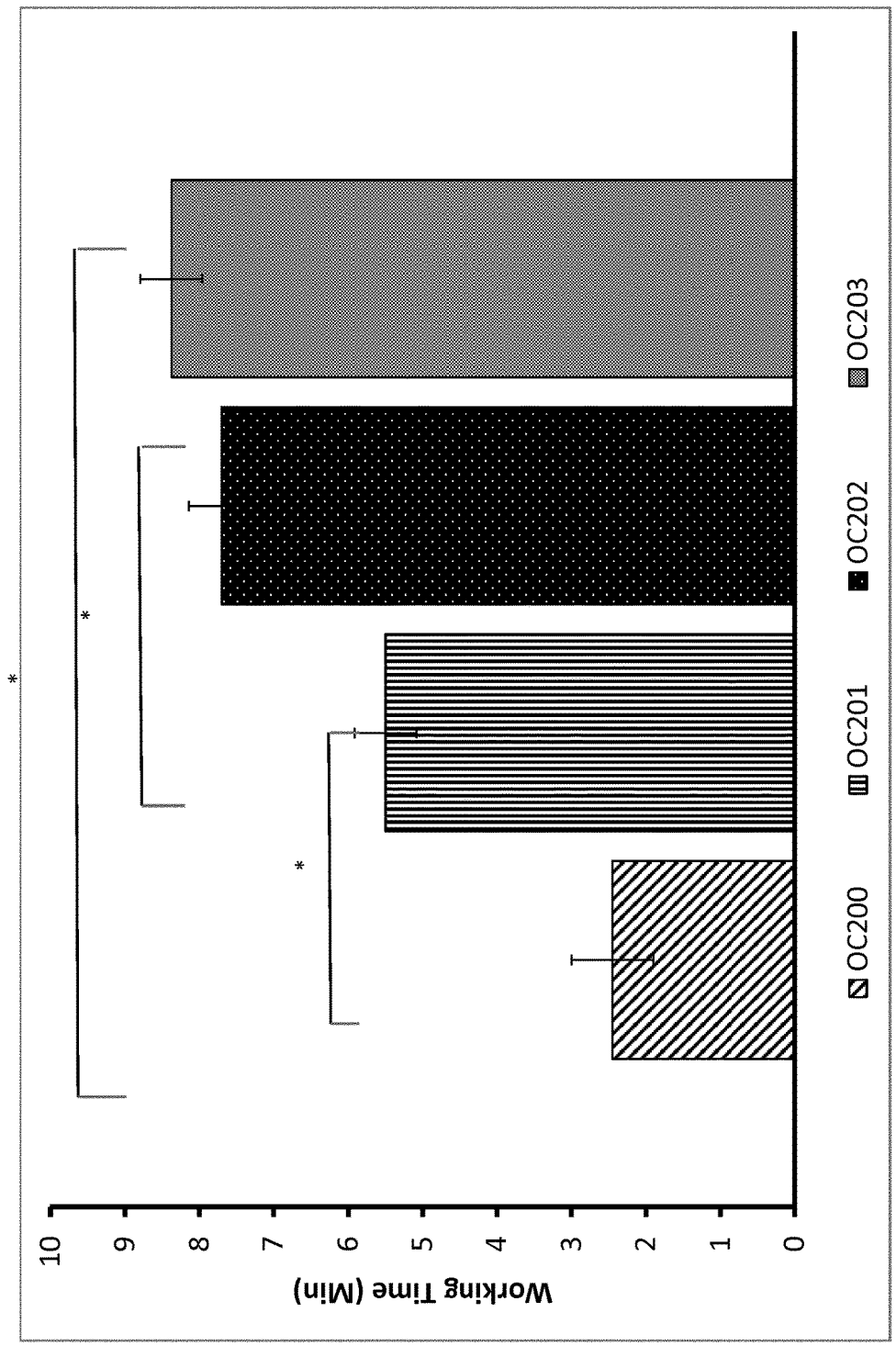
FIG. 8 shows comparisons in working times of hydrogel composite samples with different glass formulations.
Figure 9:
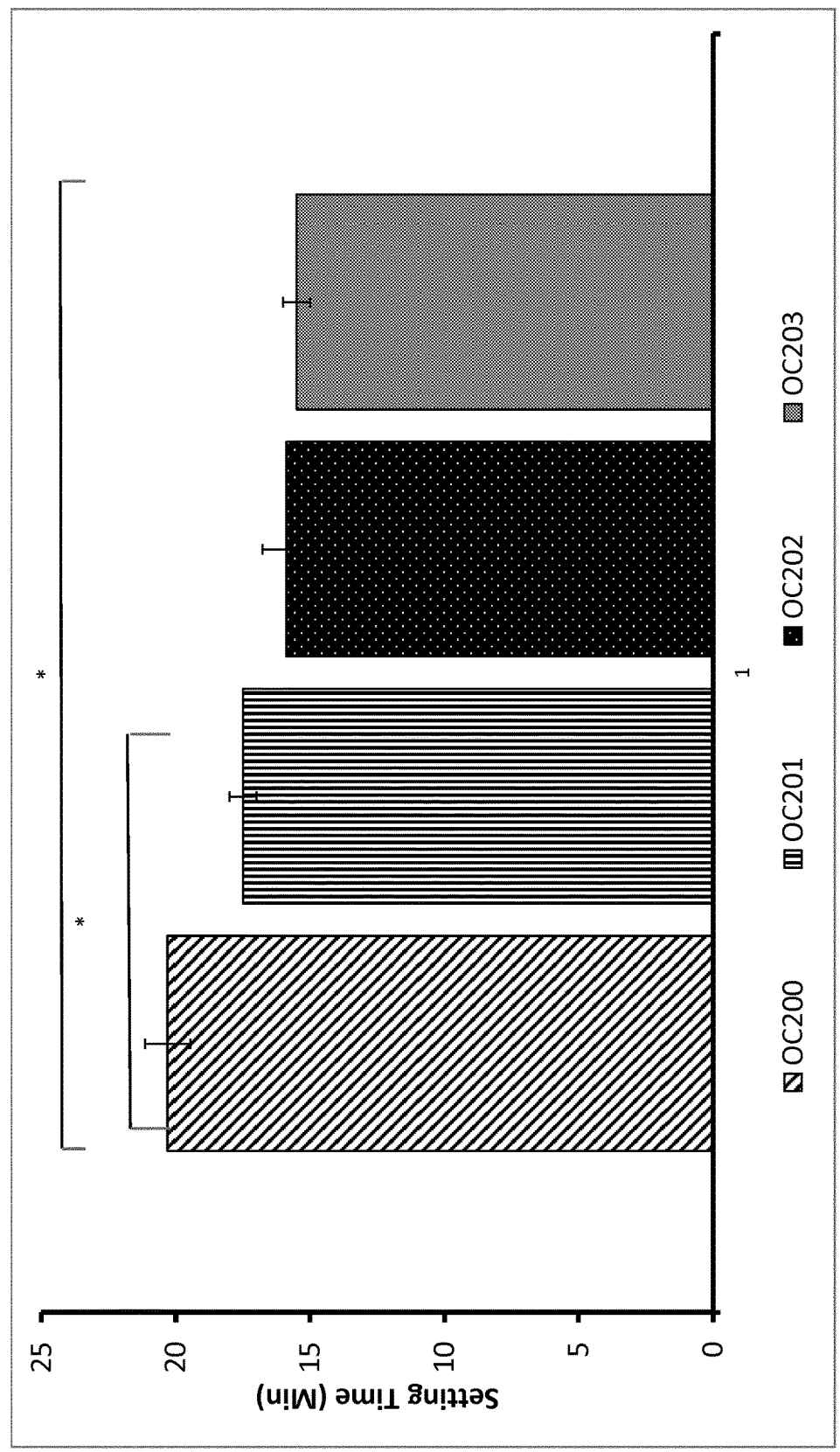
FIG. 9 shows comparisons in setting times of hydrogel composite samples with different glass formulations.

As can be observed from FIGS. 8 & 9, replacing aluminium with gallium in the glass appears to increase the working time and decrease the setting time of the gel.

Figure 10:
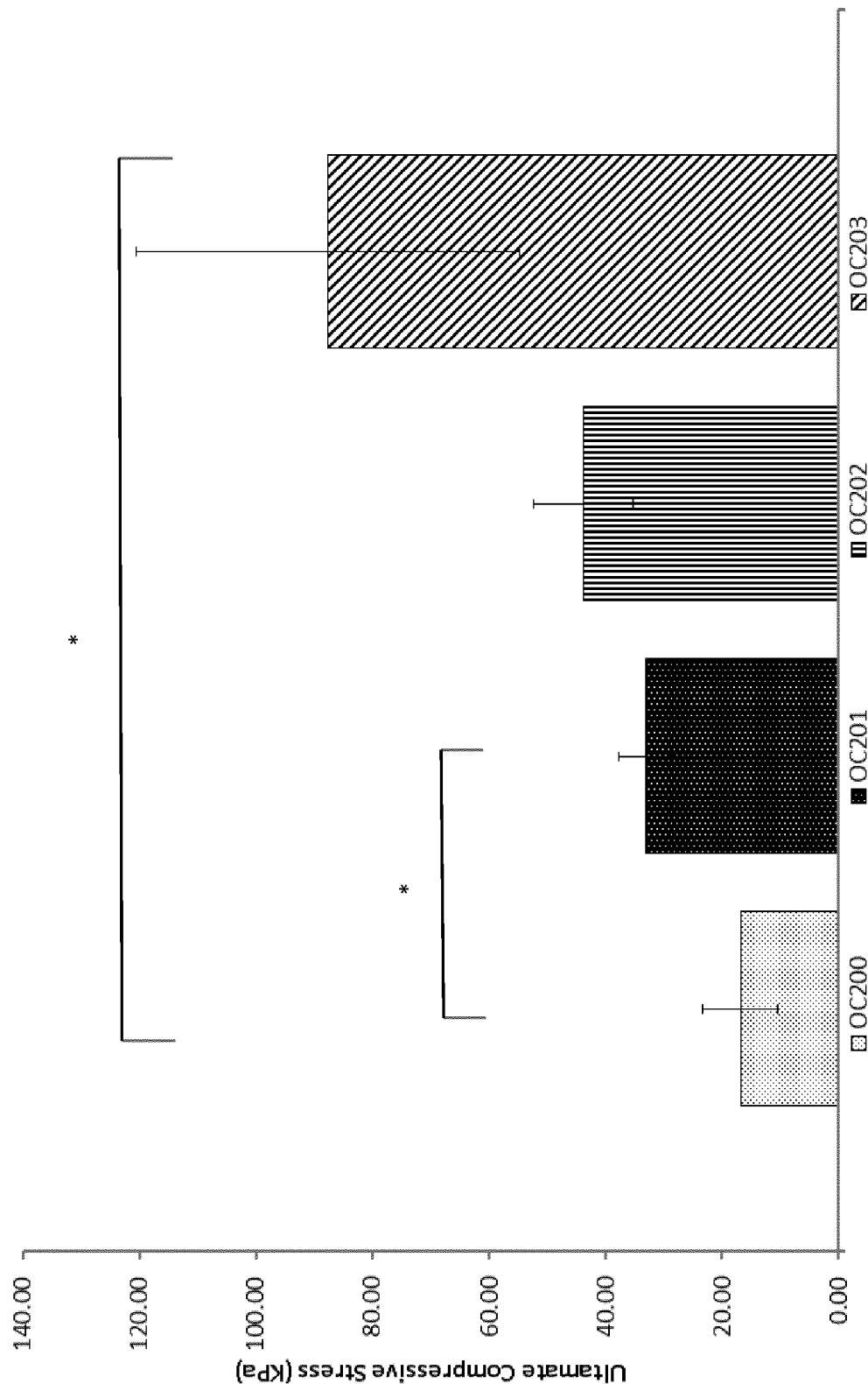
FIG. 10 shows comparisons in compressive strength of different glass compositions produced from 2 wt. % potassium alginate.
Figure 11:
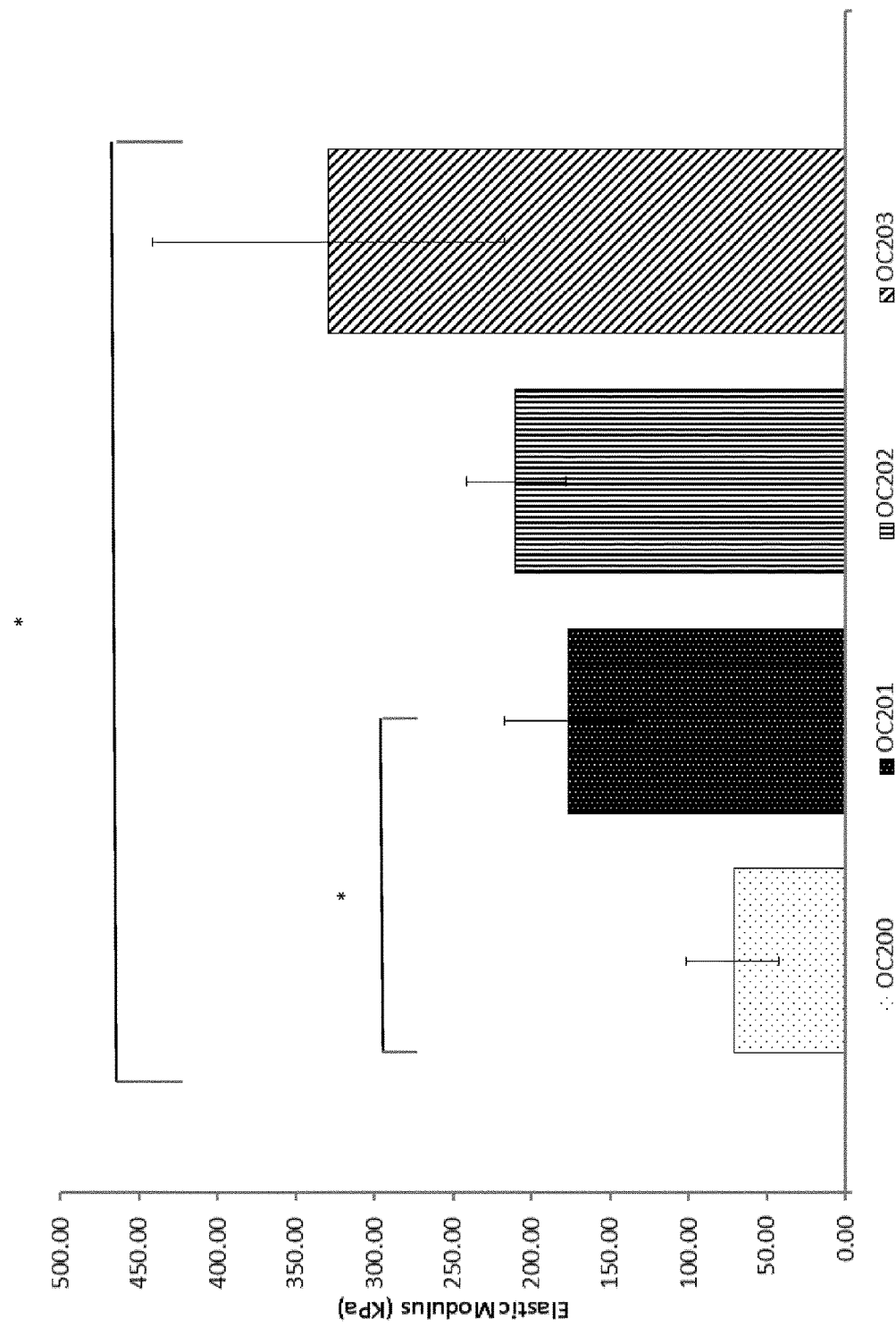
FIG. 11 shows comparisons in elastic modulus of different glass compositions produced from 2 wt. % potassium alginate.

As can be seen from FIG. 10 and FIG. 11, both ultimate compression strength and Young's modulus increase approximately linearly with Ga/Al ratio, with the gallium only gel exhibiting strengths approximately 4 times those of the gallium free gel. Compressive strength significantly increases with increased Ga/Al ratio over the range of materials examined (p=0.0001). Similar to the compressive strength, the Young's modulus of the material increased significantly with Ga/Al ratio over the range examined (p=0.0001), with the gallium only gel exhibiting a modulus of approximately 4 times those of the gallium free gel.

Figure 12:
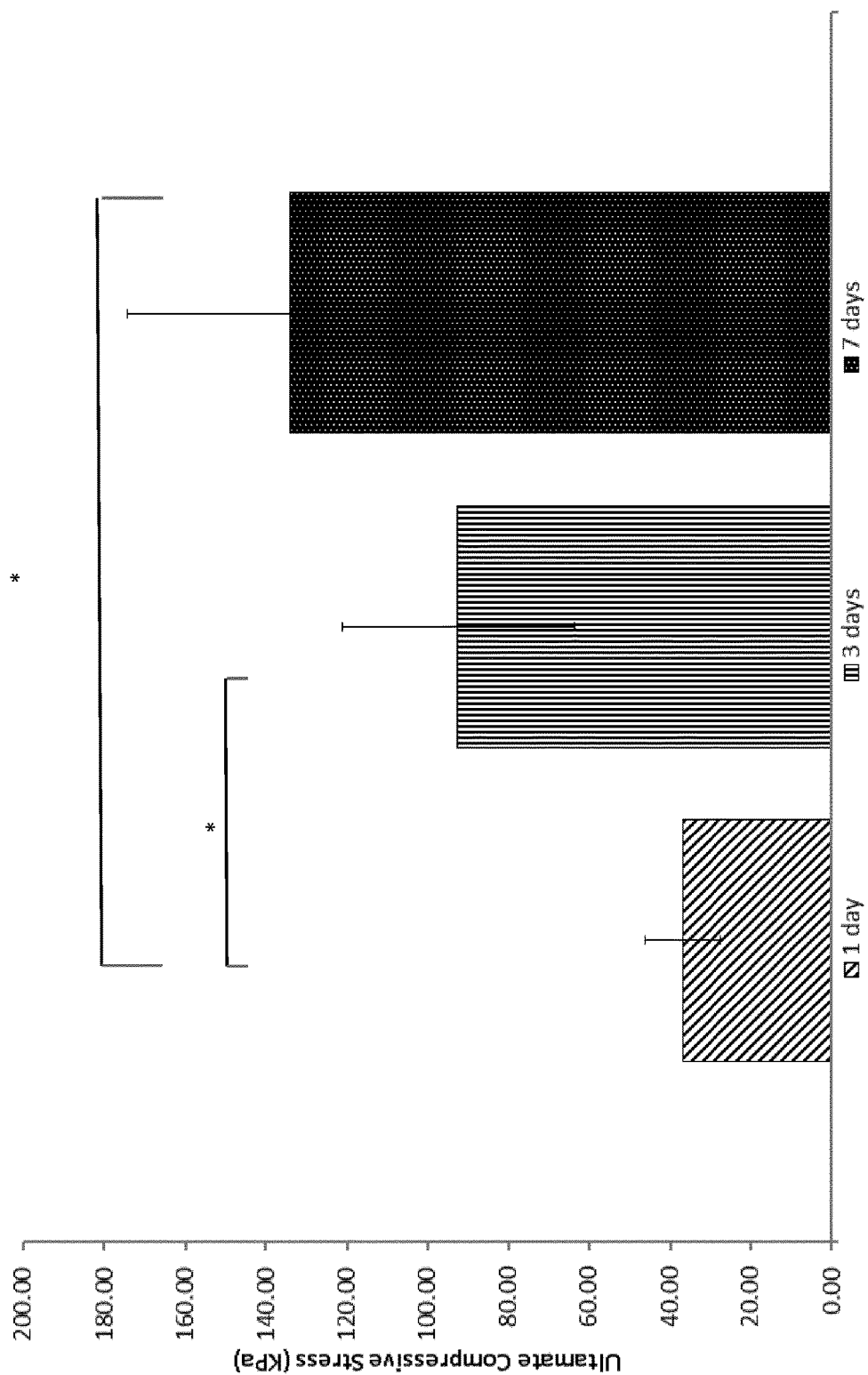
FIG. 12 shows how the compressive strength of a glass formulation produced from 2 wt. % potassium alginate in accordance with the present teaching varies as a function of time.
Figure 13:
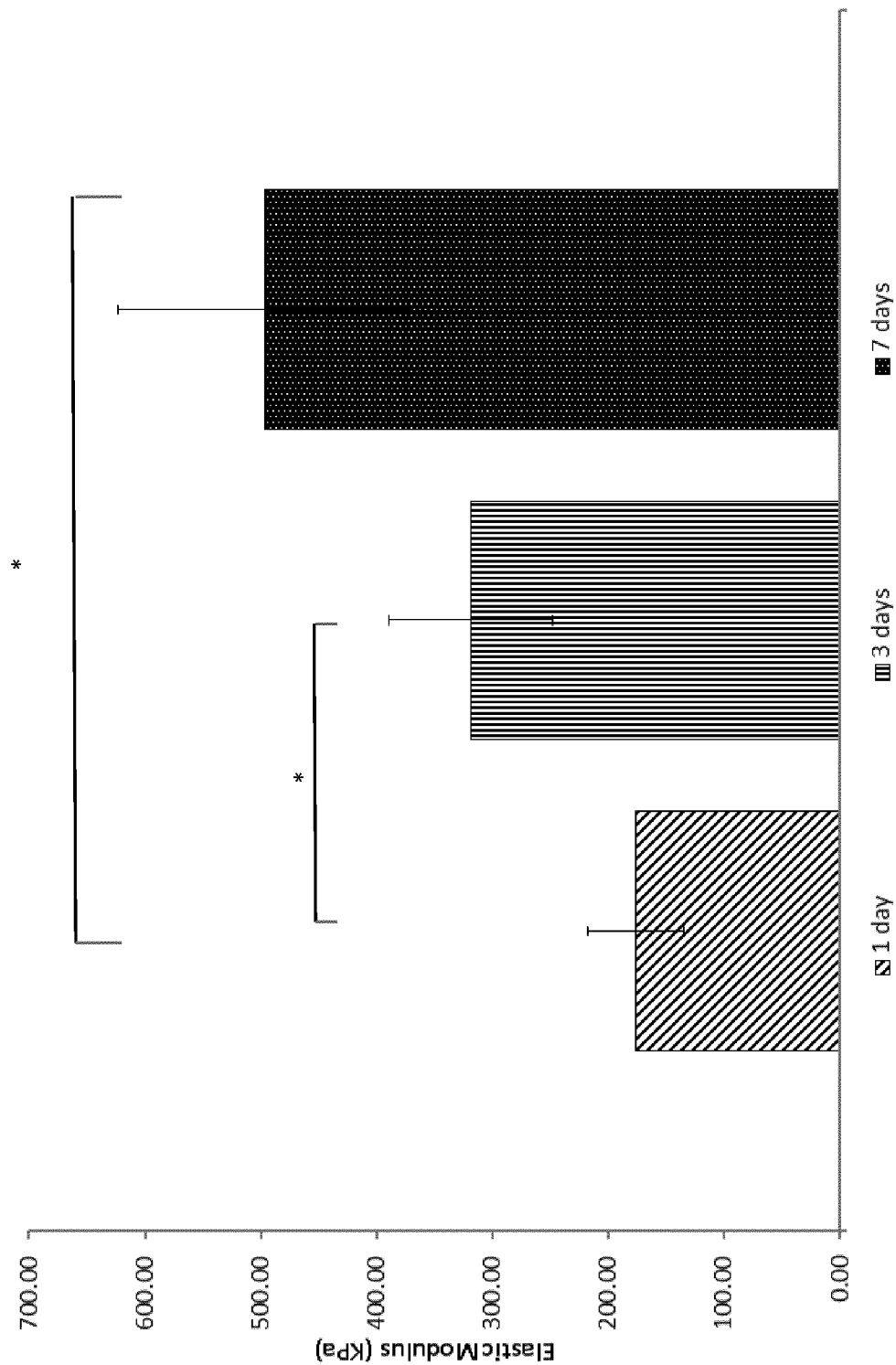
FIG. 13 shows how the elastic modulus of a glass formulation produced from 2 wt. % potassium alginate in accordance with the present teaching varies as a function of time.

As can be seen from FIG. 12 and FIG. 13, there is a significant increase in both strength and elastic modulus with time across the groups, with both strength and modulus increasing significantly between 1 and 7 days. This increase in strength of the alginate is advantageous for applications per the present teaching and justifies the judicious selection of this alginate as opposed to calcium alginate gels which would degrade over time in saline solutions due to the exchange of calcium ions for sodium and potassium ions, weakening the gels. An alginate provided in accordance with the present teaching reacts differently in that the glass particles embedded in the gel continue to release ions and increase crosslink density in the gel over time, increasing both its strength and elastic modulus.

The above experimental results demonstrate that a gallium glass per the present teaching forms tetrahedral structures, which maintain a high content of trivalent ions while maintaining high network connectivity, slow reactivity and maintaining a silicate glassy network. This glass reacted slowly enough with an alginate polymer solution to be injectable, while setting within 30 minutes of mixing. Bonds continued to develop in the gel up to 24 hours after setting, as shown by FTIR analysis and strength of the gel continued to increase with time up to 7 days. Substitution of aluminium for gallium lengthened working times, shortened setting times and improved strength and stiffness. These novel gels did not appear to induce any platelet adhesion or activation and eluents from the gels did not result in any significant cell death for either BASMCs or BAECs. These gels exhibit potential for applications of delivery into a blood contact environment.

Figure 14:
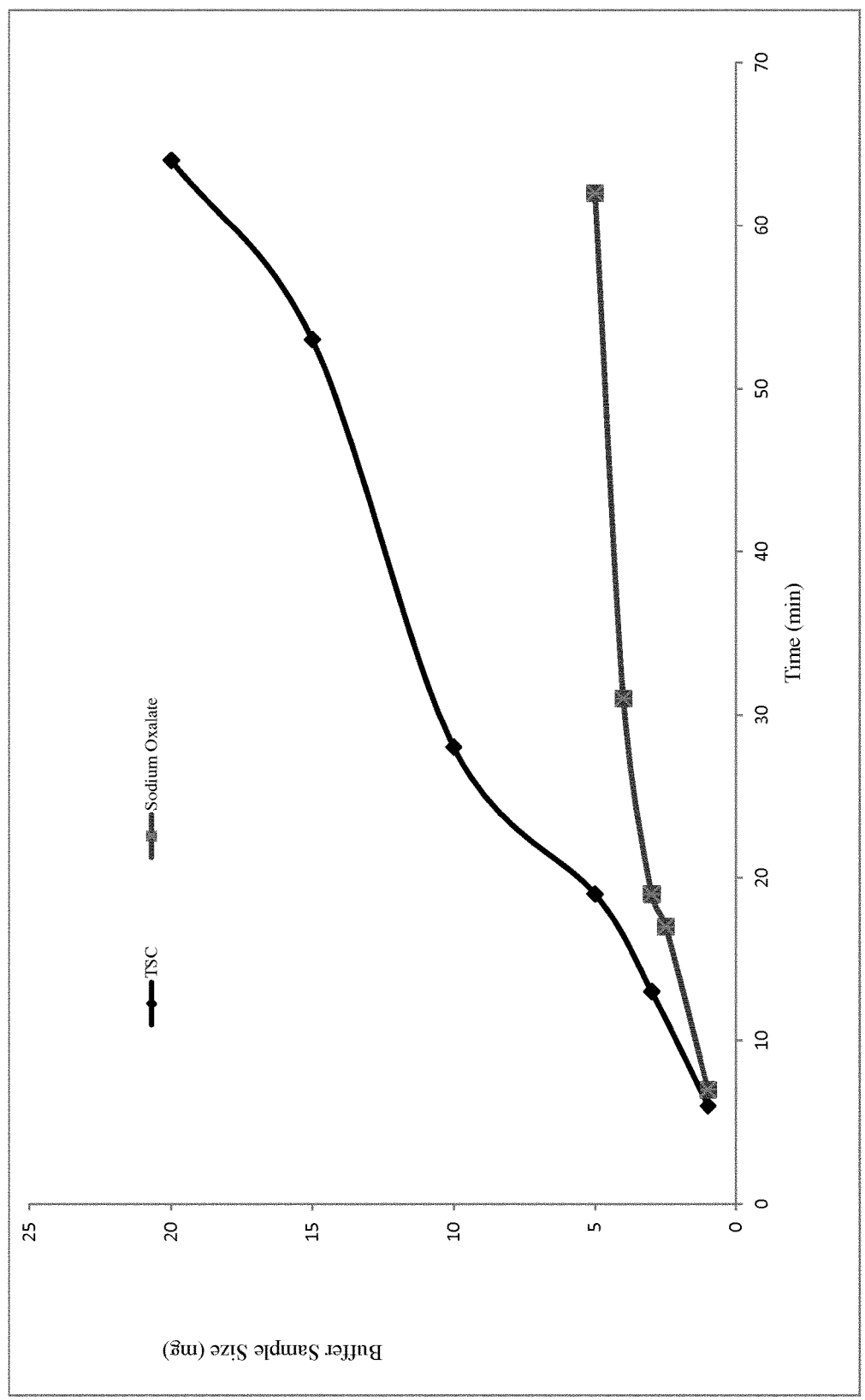
FIG. 14 shows the effect of additions of various modifying agents on the working time of the gel.
Figure 15A:
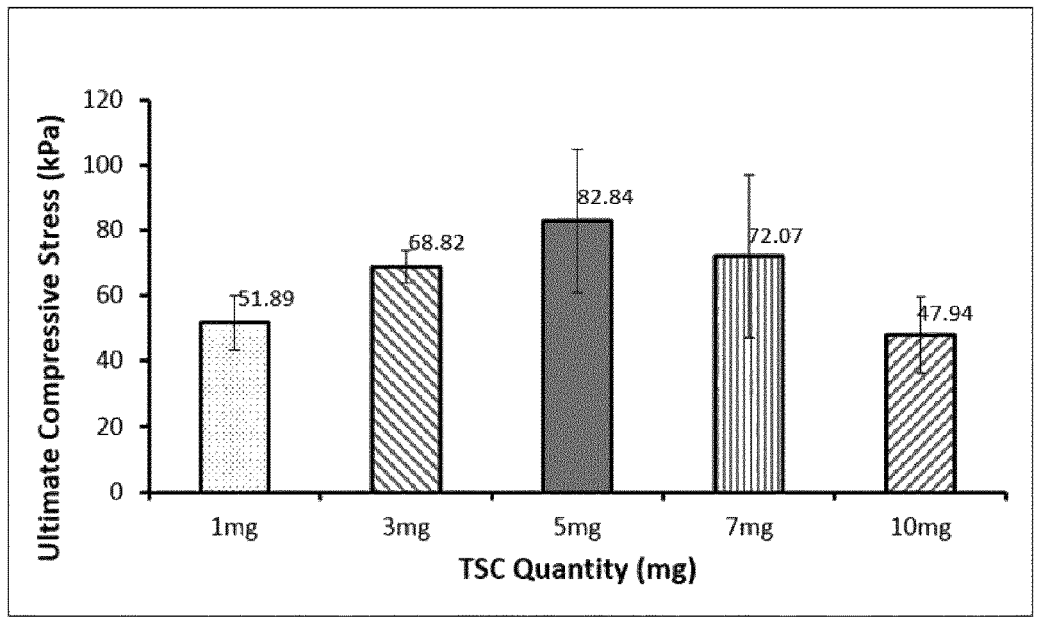
FIG. 15A shows the effect of varying TSC concentration on compressive strength and FIG. 15B shows the effect of varying sodium oxalate concentration on compressive strength.
Figure 15B:
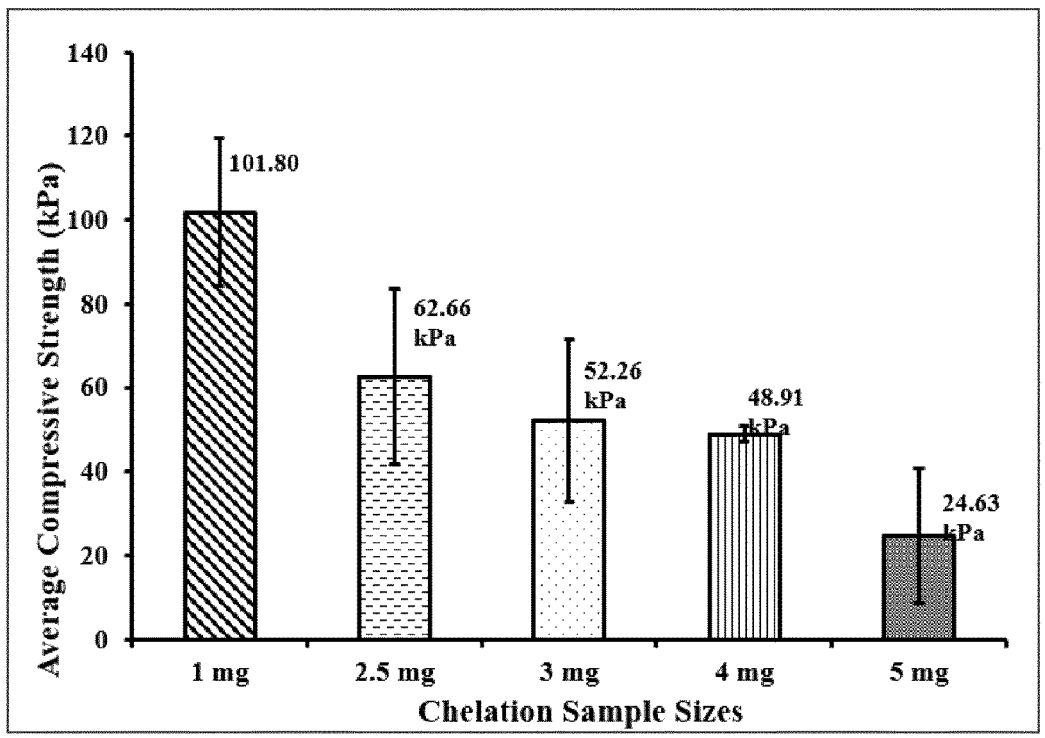

It is possible to change the properties of the composite gel by adding in additional constituents into the composition. The present inventors have identified that trisodium citrate (TSC) and sodium oxalate are particularly advantageous for use in modifying the reaction rate for this gel system. The effect of the addition of varying quantities of these compounds on gel working time is depicted in FIG. 14. As can be observed from FIGS. 15A and 15B, TSC addition up to 10 mg (in the context of a solution of 600 microliters of 2% alginate and 600 microliters of 9.2% glass solution (in water) with 0.05 g GDL) significantly increased the working time of the gel without significantly affecting compressive strength.

It will be appreciated that a composition provided in accordance with the present teaching provides a number of advantages including:
1) The novel glass composition, which allows a controlled setting reaction, without the leaching of toxic ions/radicals;
2) The combination of this novel glass composition with the alginate polymer, allowing for a flexible set composite material;
3) The glass and alginate can be combined in a particular manner and with additional reaction rate controlling species to further optimise the handling characteristics.

The use of a composition per the present teaching in the treatment of intra-cranial aneurysms requires the location of the composition within an aneurysm so as fill the aneurysm and prevents rupture. To facilitate the filling of the aneurysm, a compliant balloon may be placed adjacent to the aneurysm and inflated, as with endovascular coiling. The hydrogel will then be injected through a micro catheter into the aneurysm whilst the inflated balloon prevents leakage of the filler into the blood stream. To allow for delivery and setting an optimum working time of between 10 and 30 minutes has been determined for the novel hydrogel, based on discussion with clinical collaborators. In addition, the novel hydrogel must be set within a maximum of 5 minutes following injection based on the maximum inflation time for a balloon in the cerebral vasculature. Once the gel has set, then the balloon may be deflated.

While the composition may be advantageously employed in the treatment of aneurysms, it may be used in other biomaterials or tissue engineering applications, such as vascular grafts, scaffolds for the production of tissue engineered vessels, orthopaedic bone void fillers, cartilaginous tissue fillers, etc. It could also have applications outside of cerebral vessels, such as in abdominal aortic aneurysms.

Another application of a glass provided in accordance with the present teaching is in the field of hypoxia. Hypoxia induces stem cell recruitment, angiogenesis and stem cell differentiation. It can prevent biochemical factors from degrading, such as hypoxia inducible factor 1 (HIF-1), and can encourage release of other biochemical factors, such as Vascular Endothelial Growth Factor (VEGF). VEGF is central in the establishment and repair of blood vessel networks and encouraging angiogenesis and subsequent tissue regeneration in scaffold materials. A glass provided in accordance with the present teaching can be configured to release large amounts of gallium ions in vitro. Eluents from these novel materials have also been shown to increase endothelial cell metabolism in a dose dependent manner. It is hypothesised that the mechanism of action in this regard is via the hypoxia pathway. Gallium has a tendency to act in a similar manner to iron in vivo and is complexed with transferrin and taken in by cells. However, within the cell, unlike iron, gallium cannot be converted from a trivalent form to a divalent form which is essential to many of the functions of iron. As a result the cells become iron deficient. Iron insufficiency induces a hypoxia in tissues due to the strong link between iron and oxygen metabolism. This may subsequently result in upregulation of HIF-1α in cells and subsequent increase in cellular metabolism and release of VEGF.

This therapeutic response induced by materials provided in accordance with the present teaching may be beneficial for tissue engineering applications, both for encouraging and controlling the recruitment and differentiation of resident stem cells and for encouraging proliferation of seeded cells, either in vivo or in vitro. This may also be a valuable therapeutic response for the treatment of issues such as peripheral vascular disease (PVD), wherein a material may be injected into the vessel, in proximity to the vessel or as a coating on some device for treatment of PVD (e.g. stent).

Other applications of a composite glass gel as described above may include tumour embolization, however, for some embolization techniques, such as liver tumour embolization the formulation will need to be altered to allow complete resorption of the material to prevent tissue damage and organ failure.

Transcatheter Arterial Chemoembolization (TACE) is often carried out for the treatment of Hepatocellular Carcinoma (HCC). This technique uses anticancer agents (such as doxorubicin, epirubicin, aclarubicin, etc) mixed with a Lipiodol® (iodine added to ethyl ester of poppy seed oil), which is injected into the diseased tissue. This is typically followed by injection of gelatin sponge or micron sized PVA embolization particles into the hepatic artery. The combination of anticancer agent released from the oil and the decreased blood supply cause tumour shrinkage. However, due to poor loading and instability of the hydrophilic drugs in the oil this approach results in rapid release of the drugs (half-life: 1 hr). Currently, with this approach, the survival gain of TACE is marginal, as the HCC is usually hyper-vascular and is fed by supplies other than the hepatic artery resulting in recurrence of the residual tumour. Also, embolization of the hepatic artery causes ischemic liver tissue damage, often resulting in liver failure. However, recent studies have shown that use of smaller microcatheters (<2 French) can be used to selectively embolize tumour blood supplies, resulting in a significantly lower recurrence rate and less native tissue damage. The present inventors have realised that a glass composition per the present teaching is ideal for this application due to its ability to be injected through small diameter catheters, as well as its therapeutic potential.

A number of embolization agents are on the market, including N-butyl cyanoacrylate (NCBA), polyvinyl alcohol (PVA) microspheres, Gelfoam® (porcine fat tissue), balloons and drug-eluting beads (DEB) are the main competitors. However, none of these embolics fully overcome the problems associated with TACE, including rapid release of chemotherapeutics, damage to the native liver tissue as a result of ischemia and reperfusion injuries. The development of drug-eluting particles has aided the sustained delivery of chemotherapeutics, with PVA-based DC Beads® exhibiting doxorubicin half-life releases of 6.25 days, however, embolic beads are difficult to control and often reflux, blocking unintended arteries or causing pulmonary embolism. Additionally, these beads do not infiltrate the capillaries of the tumour as well as low viscosity fluids like Lipiodol® and degradation/recanalization rates of PVA particles are unpredictable, lasting from a week to several months.

Using a glass composition per the present application it is possible to provide a low viscosity drug eluting, degradable embolization agent which will match or better release rates from commercial particle-based embolics and have advantageous ancillary effects, resulting in a product that delivers better clinical outcomes. This embolization gel will continuously release gallium ions, which have been shown to induce apoptosis in cancer cell lines. Gallium has also been shown to reduce reactive oxygen species (ROS) in biological fluids and reduce ischemic damage following reperfusion.

The material can be developed by modifying the formulation of the described glass to allow for a more fully degradable glass by introducing increased quantities of phosphorous or by adding sodium, potassium or boron to the glass formulation.

Additionally, the alginate can be made degradable by partially oxidising the chains using techniques which will be familiar to those of skill in the art.

Therefore it will be appreciated and understood that a glass composition per the present teaching may be used in a number of biomedical applications and it is not intended to limit the present teaching to any one set of applications or uses except as may be deemed necessary in the light of the following claims.

The invention claimed is:

1. A medical application treatment kit comprising a first part comprising a polymer matrix and a second part comprising a gallium silica based glass composition having an acid labile tetrahedral structure, the first part and the second part being combinable to form an ionically crosslinked glass polymer matrix composition wherein gallium from the glass composition is cross linked into and sets the polymer matrix within the human body, wherein the second part comprises a structure of the form:

$$X-Ga_2O_3-SiO_2-Y-Z$$

where:
- X is an oxide of calcium, barium, lanthanum, strontium, beryllium, magnesium, radium or zinc;
- Y is an oxide of phosphorous or boron; and
- Z is a chloride salt provided in the form of one or more of $CaCl_2$, $BaCl_2$, $SrCl_2$, $MgCl_2$, $NH_4Cl$, $ZnCl_2$, $GaCl_3$, LiCl, NaCl or KCl.

2. The kit of claim 1 wherein the second part comprises oxides of gallium, silicon and calcium.

3. The kit of claim 2 wherein gallium, silica, phosphorous and calcium are provided in molar ratios of $0.01 \leq Ga/(Si+P) \leq 1.0$ and $0.5 \leq Ca/Ga \geq 2.0$, respectively.

4. The kit of claim 2 wherein gallium, silica, phosphorous and calcium are provided in molar ratios of $0.1 \leq Ga/(Si+P) \leq 0.7$ and $1.0 \leq Ca/Ga \geq 2.0$, respectively.

5. The kit of claim 2 wherein the oxides of gallium, silica, phosphorous and calcium are provided in molar ratios of $0.2 \leq Ga/(Si+P) \leq 0.4$ and $1.2 \leq Ca/Ga \geq 2.0$, respectively.

6. The kit of claim 1 wherein the second part comprises a structure of the form:

$CaO-Ga_2O_3-SiO_2-P_2O_5-CaCl_2$, where the Ca is optionally substituted by barium, lanthanum, strontium, beryllium, magnesium, radium or zinc.

7. The kit of claim 1 wherein the first part is a hydrogel matrix.

8. The kit of claim 7 wherein the hydrogel is an alginate hydrogel.

9. The kit of claim 7 wherein the hydrogel is a potassium alginate hydrogel.

10. The kit of claim 1 comprising at least one of trisodium citrate, TSC, and sodium oxalate.

11. The kit of claim 1 wherein the medical application is treatment of defects in a vascular network.

12. The kit of claim 1 wherein the medical treatment is treatment of one or more of: arteriovenous malformations (AVMs), dural fistulas (DAVFs), tumour embolization, treatment for peripheral vascular disease or cerebral aneurysms.

13. The kit of claim 1 wherein the medical treatment is tissue engineering or embolization.

14. The kit of claim 1 wherein the ionically crosslinked glass polymer matrix composition operably forms a biocompatible, mechanically stable, flexible material, providing controlled release of ions within the human body.

15. A method of treating a defect in a vascular structure, said vascular structure having a lumen and a wall, said method comprising the steps of:
a) introducing a gallium-based glass composition of claim 1 into the defect; and
b) allowing the gallium based glass composition to set and form a substantially solid mass within the defect.

16. The method of claim 15 wherein the introducing the gallium-based glass composition comprises providing an inflatable balloon within the aneurysm, inflating the balloon and filling the balloon with a liquid form of the gallium-based glass composition.

17. The method according to claim 15 wherein the introducing step comprises inserting a catheter into the defect and using the catheter to deliver the glass composition into the defect.

18. The method of claim 15 wherein the allowing the gallium based glass composition to set comprises cross linking gallium from the glass composition into a polymer matrix so as form an ionically crosslinked glass polymer matrix composition.

19. The method of claim 18 wherein the matrix comprises a potassium alginate hydrogel.

20. A method of forming an ionically crosslinked glass polymer matrix composition of claim 1 within the human body, the method comprising:
a. providing a polymer matrix;
b. providing a gallium silica based glass composition, the glass composition having an acid labile tetrahedral structure
c. combining the polymer matrix with the glass composition, the combining affecting a release of gallium from the glass through an acid reaction so as to allow gallium from the glass composition cross link into the polymer matrix so as to affect a setting of the glass polymer matrix composition.

21. The method of claim 20 wherein the combining provides a mixture having a working time period of 10 to 30 minutes, the setting period being in the range 1-5 minutes after completion of the working time.

22. The method of claim 20 comprising acid washing the gallium silicate glass composition to modify wettability and mixing properties of the composition.

23. The method of claim 20 wherein the polymer matrix comprises an alginate.

24. The method of claim 23 wherein the alginate is a polysaccharide composed of β-D-mannuronic acid (M) and α-l-guluronic acid (G), giving the alginate a M/G block structure having an ability to gel when the G-blocks are cross-linked with multivalent ions.

25. The method of claim 24 wherein the alginate has a molecular weight of 700 kDa and is provided at a concentration of about 4.5%.

* * * * *